(12) United States Patent
Ericsson

(10) Patent No.: US 7,883,848 B2
(45) Date of Patent: Feb. 8, 2011

(54) REGULATION ANALYSIS BY CIS REACTIVITY, RACR

(75) Inventor: Olof Ericsson, Uppsala (SE)

(73) Assignee: Olink AB, Uppsala (SE)

( * ) Notice: Subject to any disclaimer, the term of this patent is extended or adjusted under 35 U.S.C. 154(b) by 1029 days.

(21) Appl. No.: 11/483,825

(22) Filed: Jul. 10, 2006

(65) Prior Publication Data
US 2007/0020669 A1    Jan. 25, 2007

Related U.S. Application Data

(60) Provisional application No. 60/697,415, filed on Jul. 8, 2005.

(51) Int. Cl.
  C12Q 1/68        (2006.01)
  C12P 19/34       (2006.01)
  C07H 21/02       (2006.01)
  G01N 33/566      (2006.01)

(52) U.S. Cl. .................. 435/6; 435/91.2; 536/23.1; 436/501

(58) Field of Classification Search ............... None
See application file for complete search history.

(56) References Cited

U.S. PATENT DOCUMENTS

| | | | |
|---|---|---|---|
| 6,692,918 B2* | 2/2004 | Kurn | 435/6 |
| 6,878,515 B1 | 4/2005 | Landegren | |
| 2002/0051986 A1 | 5/2002 | Baez et al. | |
| 2003/0082830 A1 | 5/2003 | Schreiber et al. | |
| 2006/0246450 A1* | 11/2006 | Franch et al. | 435/6 |
| 2009/0011957 A1* | 1/2009 | Gouliaev et al. | 506/26 |
| 2009/0203530 A1* | 8/2009 | Liu et al. | 506/1 |

FOREIGN PATENT DOCUMENTS

WO    WO 2005026387 A1 *    3/2005

OTHER PUBLICATIONS

Guille et al. Methods for the analysis of DNA-protein interactions. Molecular Biotechnology 8(1):35-52, Aug. 1997.*
U.S. Appl. No. 11/011,438, filed Oct. 20, 2005, Landegren.
U.S. Appl. No. 09/785,657, filed May 30, 2002, Landegren et al.
U.S. Appl. No. 10/496,385, filed Jan. 6, 2005, Fredriksson.
Burbulis, I, et al. Using protein-DNA Chimeras to detect and count small numbers of molecules. Nat Methods. Jan. 2005; 2(1):31-37 e-pub: Dec. 21, 2004.
Duffy, S. et al. site-specific enzymatic biotinylation of recombinant proteins in Spodoptera frugiperda cells using biotin acceptor peptides. Anal Biochem. Sep. 10, 1998:262(2):122-28.
Fan JB, et al. "A versatile assay for high-throughput gene expression profiling on universal array matrices" Genome Res. May 2004;14(5):878-85.
Fredriksson S, Gullberg M, Jarvius J, Olsson C, Pietras K, Gustafsdottir SM, Ostman A, Landegren U. Protein detection using proximity-dependent DNA ligation assays. Nat Biotechnol. May 2002;20(5):473-7.
Gullberg M, Gustafsdottir SM, Schallmeiner E, Jarvius J, Bjarnegard M, Betsholtz C, Landegren U, Fredriksson S. Cytokine detection by antibody-based proximity ligation. Proc Natl Acad Sci U S A. Jun 1, 2004;101(2)8420-4. Epub May 21, 2004.
Gunderson KL, Steemers FJ, Lee G, Mendoza LG, Chee MS. A genome-wide scalable SNP genotyping assay using microarray technology. Nat Genet. May 2005;375:549-54. Epub Apr. 17, 2005.
Gunderson KL, Kruglyak S, Graige MS, Garcia F, Kermani BG, Zhao C, Che D, Dickinson T, Wickham E, Bierle J, Doucet D, Milewski M, Yang R, Siegmund C, Haas J, Zhou L, Oliphant A, Fan JB, Barnard S, Chee MS. Decoding randomly ordered DNA arrays. Genome Res. May 2004;14(5):870-7. Epub Apr. 12, 2004.
Hanes J, Pluckthun A. In vitro selection and evolution of functional proteins by using ribosome display. Proc Natl Acad Sci U S A. May 13, 1997;94(10):4937-42.
Hardenbol P, Baner J, Jain M, Nilsson M, Namsaraev EA, Karlin-Neumann GA, Fakhrai-Rad H, Ronaghi M, Willis TD, Landegren U, Davis RW. Multiplexed genotyping with sequence-tagged molecular inversion probes. Nat Biotechnol. Jun. 2003;21(6):673-8. Epub May 5, 2003.
Hatch A, Sano T, Misasi J, Smith CL. Rolling circle amplification of DNA immobilized on solid surfaces and its application to multiplex mutation detection. Genet Anal. Apr. 1999;15(2):35-40.
Kanan MW, Rozenman MM, Sakurai K, Snyder TM, Liu DR. Reaction discovery enabled by DNA-templated synthesis and in vitro selection. Nature. Sep. 30, 2004;431(7008):545-9.
Keppler A, Kindermann M, Gendreizig S, Pick H, Vogel H, Johnsson K. Labeling of fusion proteins of O6-alkylguanine-DNA alkyltransferase with small molecules in vivo and in vitro. Methods. Apr. 2004;32(4):437-44.
Landegren U, Kaiser R, Sanders J, Hood L. A ligase-mediated gene detection technique. Science. Aug. 26, 1988;241(4869):1077-80.
Lizardi PM, Huang X, Zhu Z, Bray-Ward P, Thomas DC, Ward DC. Mutation detection and single-molecule counting using isothermal rolling-circle amplification. Nat Genet. Jul. 1998;19(3):225-32.
Lyamichev V, Brow MA, Dalberg JE. Structure-specific endonucleolytic cleavage of nucleic acids by eubacterial DNA polymerases. Science. May 7, 1993;260(5109):778-83.

(Continued)

Primary Examiner—Samuel C Woolwine
(74) Attorney, Agent, or Firm—Porter, Wright, Morris & Arthur, LLP

(57) ABSTRACT

Methods of detecting affinity interactions between at least two molecules of interest are provided. The method comprises: a. forming a plurality of interactors by coupling each molecule of interest with at least one nucleic acid moiety comprising an identification sequence element and at an association element; b. promoting an association between at least two nucleic acid moieties from different interactors to form a plurality of unique associated oligonucleotides, wherein each nucleic acid moiety may form more than one unique associated oligonucleotide, and wherein each unique associated oligonucleotide comprises at least two identification sequence elements derived from the at least two nucleic acid moieties; c. selecting the plurality of unique associated oligonucleotides; and d. subjecting the selected associated oligonucleotides to an analysis that permits detection of the at least two identification sequence elements. Similar methods directed to detecting functional interactions, libraries of interactors employable in the present methods, and kits comprising those libraries are also provided.

20 Claims, 9 Drawing Sheets

OTHER PUBLICATIONS

Odegrip R, Coomber D, Eldridge B, Hederer R, Kuhlman PA, Ullman C, FitzGerald K, McGregor D. CIS display: In vitro selection of peptides from libraries of protein-DNA complexes. Proc Natl Acad Sci U S A. Mar. 2, 2004;101(9):2806-10. Epub Feb. 23, 2004.

Reiersen H, Lobersli I, Loset GA, Hvattum E, Simonsen B, Stacy JE, McGregor D, Fitzgerald K, Welschof M, Brekke OH, Marvik OJ. Covalent antibody display—an in vitro antibody-DNA library selection system. Nucleic Acids Res. Jan. 14, 2004;33(1):e10.

Southworth MW, Amaya K, Evans TC, Xu MQ, Perler FB. Purification of proteins fused to either the amino or carboxy terminus of the Mycobacterium xenopi gyrase A intein. Biotechniques. Jul. 1999;27(1):110-4, 116, 118-20.

Takeda S, Tsukiji S, Nagamune T. Site-specific conjugation of oligonucleotides to the C-terminus of recombinant protein by expressed protein ligation. Bioorg Med Chem Lett. May 17, 2004;14(10):2407-10.

Tan DS, Foley MA, Shair MD, Schreiber SL. Stereoselective synthesis of over two million compounds having structural features both reminiscent of natural products and compatible with miniaturized cell-based assays.

Wilson DS, Keefe AD, Szostak JW. The use of mRNA display to select high-affinity protein-binding peptides. Proc Natl Acad Sci U S A. Mar. 27, 2007;98(7):3750-5. Epub Mar. 13, 2001.

Yeakley JM, Fan JB, Doucet D, Luo L, Wickham E, Ye Z, Chee MS, Fu XD. Profiling alternative splicing on fiber-optic arrays. Nat Biotechnol. Apr. 2002;20(4):353-8.

* cited by examiner

SEQUENCE LISTING

<160> NUMBER OF SEQ ID NOS: 30

<210> SEQ ID NO 1
<211> LENGTH: 50
<212> TYPE: DNA
<213> ORGANISM: artificial
<220> FEATURE:
<223> OTHER INFORMATION: chemically synthesized

<400> SEQUENCE: 1
tctctctctc tctctctctc gatgaatgtc gtcgcaacac cgtccatacg     50

<210> SEQ ID NO 2
<211> LENGTH: 50
<212> TYPE: DNA
<213> ORGANISM: artificial
<220> FEATURE:
<223> OTHER INFORMATION: chemically synthesized

<400> SEQUENCE: 2
tctctctctc tctctctctc gatgaatgtc gtcgcgtatc acgttcgtcg     50

<210> SEQ ID NO 3

<211> LENGTH: 50
<212> TYPE: DNA
<213> ORGANISM: artificial
<220> FEATURE:
<223> OTHER INFORMATION: chemically synthesized

<400> SEQUENCE: 3
tctctctctc tctctctctc gatgaatgtc gtcgcctccg taatcgtggt         50

<210> SEQ ID NO 4
<211> LENGTH: 50
<212> TYPE: DNA
<213> ORGANISM: artificial
<220> FEATURE:
<223> OTHER INFORMATION: chemically synthesized

<400> SEQUENCE: 4
tctctctctc tctctctctc gatgaatgtc gtcgcaaccg tatcctcacg         50

<210> SEQ ID NO 5
<211> LENGTH: 50
<212> TYPE: DNA
<213> ORGANISM: artificial
<220> FEATURE:
<223> OTHER INFORMATION: chemically synthesized

<400> SEQUENCE: 5
tctctctctc tctctctctc gatgaatgtc gtcgcttacc ctctttcggc         50

<210> SEQ ID NO 6
<211> LENGTH: 50
<212> TYPE: DNA
<213> ORGANISM: artificial
<220> FEATURE:
<223> OTHER INFORMATION: chemically synthesized

<400> SEQUENCE: 6
tctctctctc tctctctctc ggcgcacatg gtatagtatc acgttcgtcg         50

<210> SEQ ID NO 7
<211> LENGTH: 50
<212> TYPE: DNA
<213> ORGANISM: artificial
<220> FEATURE:
<223> OTHER INFORMATION: chemically synthesized

<400> SEQUENCE: 7
tctctctctc tctctctctc ggcgcacatg gtatactccg taatcgtggt         50

<210> SEQ ID NO 8
<211> LENGTH: 50
<212> TYPE: DNA
<213> ORGANISM: artificial
<220> FEATURE:
<223> OTHER INFORMATION: chemically synthesized

<400> SEQUENCE: 8
tctctctctc tctctctctc ggcgcacatg gtataaaccg tatcctcacg         50

<210> SEQ ID NO 9
<211> LENGTH: 50
<212> TYPE: DNA
<213> ORGANISM: artificial
<220> FEATURE:
<223> OTHER INFORMATION: chemically synthesized

<400> SEQUENCE: 9
tctctctctc tctctctctc ggcgcacatg gtatattacc ctctttcggc        50

<210> SEQ ID NO 10
<211> LENGTH: 50
<212> TYPE: DNA
<213> ORGANISM: artificial
<220> FEATURE:
<223> OTHER INFORMATION: chemically synthesized

<400> SEQUENCE: 10
tctctctctc tctctctctc tgtgcgactt tctcactccg taatcgtggt        50

<210> SEQ ID NO 11
<211> LENGTH: 50
<212> TYPE: DNA
<213> ORGANISM: artificial
<220> FEATURE:
<223> OTHER INFORMATION: chemically synthesized

<400> SEQUENCE: 11
tctctctctc tctctctctc tgtgcgactt tctcaaaccg tatcctcacg        50

<210> SEQ ID NO 12
<211> LENGTH: 50
<212> TYPE: DNA
<213> ORGANISM: artificial
<220> FEATURE:
<223> OTHER INFORMATION: chemically synthesized

<400> SEQUENCE: 12
tctctctctc tctctctctc tgtgcgactt tctcattacc ctctttcggc        50

<210> SEQ ID NO 13
<211> LENGTH: 50
<212> TYPE: DNA
<213> ORGANISM: artificial
<220> FEATURE:
<223> OTHER INFORMATION: chemically synthesized

<400> SEQUENCE: 13
tctctctctc tctctctctc cgacctaatg ctacgaaccg tatcctcacg        50

<210> SEQ ID NO 14
<211> LENGTH: 50
<212> TYPE: DNA
<213> ORGANISM: artificial
<220> FEATURE:
<223> OTHER INFORMATION: chemically synthesized

<400> SEQUENCE: 14
tctctctctc tctctctctc cgacctaatg ctacgttacc ctctttcggc        50

<210> SEQ ID NO 15
<211> LENGTH: 50
<212> TYPE: DNA
<213> ORGANISM: artificial
<220> FEATURE:
<223> OTHER INFORMATION: chemically synthesized

<400> SEQUENCE: 15
tctctctctc tctctctctc gcgcctactg tgtatttacc ctctttcggc        50

<210> SEQ ID NO 16
<211> LENGTH: 63
<212> TYPE: DNA

```
<213> ORGANISM: artificial
<220> FEATURE:
<223> OTHER INFORMATION: chemically synthesized

<400> SEQUENCE: 16
aagatagcgt acagtcggca aaagagtcga gagctccgta atcgtggtaa aaagtatctg       60
ctt                                                                    63

<210> SEQ ID NO 17
<211> LENGTH: 63
<212> TYPE: DNA
<213> ORGANISM: artificial
<220> FEATURE:
<223> OTHER INFORMATION: chemically synthesized

<400> SEQUENCE: 17
aagatagcgt acagtcggca aaagagtcga gagaaccgta tcctcacgaa aaagtatctg       60
ctt                                                                    63

<210> SEQ ID NO 18
<211> LENGTH: 63
<212> TYPE: DNA
<213> ORGANISM: artificial
<220> FEATURE:
<223> OTHER INFORMATION: chemically synthesized

<400> SEQUENCE: 18
atgtcgcccg aaaaagatga atgtcgtcgc gagaggactc aaaacaacta ggtacaggta       60
tcg                                                                    63

<210> SEQ ID NO 19
<211> LENGTH: 63
<212> TYPE: DNA
<213> ORGANISM: artificial
<220> FEATURE:
<223> OTHER INFORMATION: chemically synthesized

<400> SEQUENCE: 19
atgtcgcccg aaaaaggcgc acatggtata gagaggactc aaaacaacta ggtacaggta       60
tcg                                                                    63

<210> SEQ ID NO 20
<211> LENGTH: 83
<212> TYPE: DNA
<213> ORGANISM: artificial
<220> FEATURE:
<223> OTHER INFORMATION: chemically synthesized

<400> SEQUENCE: 20
gtactggctg ataatcttcc aagatagcgt acagtcggca aaagagtcga gagaacaccg       60
tccatacgaa aaagtatctg ctt                                              83

<210> SEQ ID NO 21
<211> LENGTH: 83
<212> TYPE: DNA
<213> ORGANISM: artificial
<220> FEATURE:
<223> OTHER INFORMATION: chemically synthesized

<400> SEQUENCE: 21
cccgagcagc cggagcagag aagatagcgt acagtcggca aaagagtcga gaggtatcac       60
gttcgtcgaa aaagtatctg ctt                                              83
```

<210> SEQ ID NO 22
<211> LENGTH: 83
<212> TYPE: DNA
<213> ORGANISM: artificial
<220> FEATURE:
<223> OTHER INFORMATION: chemically synthesized

<400> SEQUENCE: 22
gtcctgtgtc tgaacctgag aagatagcgt acagtcggca aaagagtcga gagttcccct    60
ctttcggcaa aaagtatctg ctt                                            83

<210> SEQ ID NO 23
<211> LENGTH: 83
<212> TYPE: DNA
<213> ORGANISM: artificial
<220> FEATURE:
<223> OTHER INFORMATION: chemically synthesized

<400> SEQUENCE: 23
atgtcgcccg aaaaatgtgc gactttctca gagaggactc aaaacaacta ggtacaggta    60
tcgtgtcgac gaggatgaag agg                                            83

<210> SEQ ID NO 24
<211> LENGTH: 83
<212> TYPE: DNA
<213> ORGANISM: artificial
<220> FEATURE:
<223> OTHER INFORMATION: chemically synthesized

<400> SEQUENCE: 24
atgtcgcccg aaaaacgacc taatgctacg gagaggactc aaaacaacta ggtacaggta    60
tcgctgtggc atgtttgtct aca                                            83

<210> SEQ ID NO 25
<211> LENGTH: 83
<212> TYPE: DNA
<213> ORGANISM: artificial
<220> FEATURE:
<223> OTHER INFORMATION: chemically synthesized

<400> SEQUENCE: 25
atgtcgcccg aaaagcgcc tactgtgtat gagaggactc aaaacaacta ggtacaggta     60
tcggtattgt gatttttaa aag                                             83

<210> SEQ ID NO 26
<211> LENGTH: 20
<212> TYPE: DNA
<213> ORGANISM: artificial
<220> FEATURE:
<223> OTHER INFORMATION: chemically synthesized

<400> SEQUENCE: 26
tagttgtttt gagtcctctc                                                20

<210> SEQ ID NO 27
<211> LENGTH: 19
<212> TYPE: DNA
<213> ORGANISM: artificial
<220> FEATURE:
<223> OTHER INFORMATION: chemically synthesized

<400> SEQUENCE: 27

-continued

```
tcggcaaaag agtcgagag                                              19

<210> SEQ ID NO 28
<211> LENGTH: 19
<212> TYPE: DNA
<213> ORGANISM: artificial
<220> FEATURE:
<223> OTHER INFORMATION: chemically synthesized

<400> SEQUENCE: 28
gagaggactc aaacaacta                                              19

<210> SEQ ID NO 29
<211> LENGTH: 29
<212> TYPE: DNA
<213> ORGANISM: artificial
<220> FEATURE:
<223> OTHER INFORMATION: chemically synthesized

<400> SEQUENCE: 29
aaaaacgggc gacataagca gatacaaaa                                   29

<210> SEQ ID NO 30
<211> LENGTH: 20
<212> TYPE: DNA
<213> ORGANISM: artificial
<220> FEATURE:
<223> OTHER INFORMATION: chemically synthesized

<400> SEQUENCE: 30
cgggcgacat aagcagatac                                             20
```

REGULATION ANALYSIS BY CIS REACTIVITY, RACR

RELATED APPLICATION

This application claims priority to U.S. Provisional application Ser. No. 60/697,415, filed on Jul. 8, 2005.

FIELD OF THE INVENTION

The invention relates to methods for detecting affinity-based interactions and functional-based interactions, and the relative strengths of those interactions between molecules of interest. Libraries of interactors are constructed wherein the interactors comprise at least one molecule of interest coupled to at least one unique nucleic acid moiety. The inventive methods allow detection, interactor identification, and determination of relative strengths of all interactions possible within a library of interactors. Kits enabling rapid and efficient application of the inventive methods are also provided.

BACKGROUND OF THE INVENTION

To identify molecular networks, information concerning at least two molecular species must be gathered since there are at least two molecules involved in any interaction. Current high throughput techniques generally resolve one of the interaction partners in a high throughput fashion while the other interaction partner is limited to much fewer species. There is a need for methods which permit high throughput screening and identification of all partners of an interaction.

The human genome contains approximately 30,000 genes, disregarding splice variants and post translational modifications this corresponds approximately to 30,000 proteins and $4.5*10^8$ possible protein pairs. In general, if there are n molecules of interest in the library, then there exists $(n^2+n)/2$ possible interaction pairs in the network. The capability of investigating vast libraries and networks like these would be greatly enhanced by the development of molecular interaction-based methods wherein high throughput information may be generated for both partners of the interaction.

To analyze complex libraries a readout platform which enables data acquisition in high throughput fashion is required. Protein analysis via micro-array techniques can be achieved by converting information about protein interactions into nucleic acid-based information, which is highly amenable to analysis with microarrays. Microarray analysis is a conventional platform which enables cost effective data generation in a high throughput manner. A method of protein interaction analysis which is successfully adapted for microarray analysis is highly desirable. The present inventors have developed such an adaptation wherein molecular interactions are detected by detecting a combination of at least two nucleic acid tags, one from each molecule, wherein at least one such combination is required for signal output in one microarray feature.

Several other approaches exist in the art which can be utilized for interaction screening, but which differ from the present inventive methods in significant ways.

Protein microarrays use micro-scale, spatial localization for identification of different molecules. The format allows detection of molecules in high throughput if target molecules in solution are investigated by probes organized on a solid phase. Targets can be labelled with a detectable function and the presence of the detectable function in one array feature reflects the presence of the target in the sample, assuming that no cross reactivity between probes are present. Examples of this approach are expression arrays and antibody arrays. The assumption when using these arrays is that each target in solution only displays affinity to one defined probe on the microarray. When investigating molecular interactions the affinities are not known per definition. To identify molecular interactions with regular microarray analysis one detectable function is required for each target in solution.

The number of detectable functions which can be resolved then becomes limiting. Generally only one or two detectable functions are used although there are approaches which potentially could resolve more they are far away from the number of molecules which can be identified by position in the array. This limits the capacity of information extraction per experiment to the number of detectable functions multiplied by the library size, e.g. if a library has 500 members and the approach can detect two detectable functions 250 arrays need to be performed to extract all possible interaction information. Further on, the microarray platform suffers from the disadvantage that one partner of the protein pair needs to be immobilized on a solid phase which potentially can disturb the interaction and/or the protein conformation. While protein microarrays permit analysis of one member of an interaction in high throughput and can provide information about interactions, the data extraction is cost and labour effective. The analysis is performed on a solid phase and interaction studies are limited by the number of resolvable detectable functions which also limits the possibility of inter- or intralibrary interaction screens.

Another known method is the yeast two hybrid system which utilizes transcription factors to investigate protein interactions. Many transcription factors contain two distinct functional regions, one which binds a specific DNA sequence and one which recruits the transcription machinery to activate a proximal gene. Yeast two hybrid systems utilize these features to investigate protein affinity interactions. One protein or protein library is fused with the DNA binding domain forming the "bait" and a second protein or protein library is joined to the activating domain forming the "prey". The fusions are constructed on the DNA level and the two constructs are then co-expressed in yeast. If two proteins which have affinity for each other are expressed in the same cell they will activate transcription. Affinity interaction can then be detected by reporter gene activation due to reconstitution of the transcription factor. The two major approaches for yeast two hybrid interaction analysis is the "array approach" and the "exhaustive screening" approach. In the array approach yeast clones expressing different baits are ordered in an array so that the identity of the protein in each clone can be deducted from position. The array is then mated with yeast expressing one prey protein of interest. The mated clones are then cultured on selective media and protein interactions can be identified without cloning and sequencing from the position of positive clones on the array. The exhaustive screening approach mate one bait clone with a library of prey proteins, the mated library is then cultured on selective media and positive clones are sequenced to identify which prey proteins have interacted with the bait. The major drawback of the exhaustive screening approach is the time and cost of sequencing all the positive clones, which combined with the high intrinsic level of false positives increase the time and cost dramatically, compared to the array approach. Hence, library-library screens are generally not considered.

While the yeast two hybrid systems are advantageous in that they are genetic systems and thus do not require protein synthesis, and they can perform high throughput of one of the interaction partners, sequencing of positive clones is necessary for high throughput library screening approaches, which, combined with an intrinsic high frequency of false positives becomes problematic.

Display techniques such as phage display, ribosome display, RNA display, SELEX, cis display and covalent display are used to isolate affinity binders from libraries. These techniques are based on a large library of potential interaction partners (binders) which are allowed to interact with one partner (target). The target is typically immobilized on a solid phase and then allowed to interact with the library of binders. Members of the library which do not bind to the target are discarded and bound members are regenerated. Then the procedure is iterated until only one or a few library members remain. These are then analysed for affinity towards the target. The different display techniques primarily differ in what molecule type is used to create the library and how the binders are regenerated. Display techniques can be used to identify affinity interactions but these are generally limited to a low number of target molecules. Some display techniques like phage display have the potential to identify interactions between libraries but the analysis of the interactions are done by cloning and sequencing which is very time consuming and labour intensive. A majority of the display techniques like e.g phage display are genetic systems and do not easily adapt to other molecules than proteins.

To enable selection of binders based on libraries other than peptide, protein or nucleic acid, libraries, DNA templated synthesis (DTS) approaches has been developed. In this technique, nucleic acids can be attached to low molecular compounds in order to establish identification of the compound after selection of a library for a desired property. If two compounds are attached to nucleic acids which are complementary, hybridization of these nucleic acids will force the two compounds in proximity and elevate the relative local concentration of the compounds. Thus, the two compounds will be more prone to react than if they were not associated. This approach has also been utilized for multi step reactions, where libraries of compounds joined to nucleic acid tags are directed to serially react with a compound attached to a template nucleic acid. The synthesized library can then be screened with respect to a desired property and selected compounds can then be identified. Further on, the identity of compounds synthesized by DTS can be identified by microarray hybridization of the nucleic acid template which directed the synthesis and to which the product is also attached.

In DTS, two molecules are forced together by using nucleic acids to allow the molecules to interact to a higher degree than if they were not brought in proximity. For example, in the DTS-based method taught by Kanan et. al (Kanan et. al Nature 2004), one of the molecules forced together is attached to a "template" nucleic acid which specifically directs the second compound by direct hybridization of the nucleic acid attached to the second molecule. Thus the "template" nucleic acid contains both tags used to identify the compounds which are forced together. To create interactions between all members of a library with n members with this approach, the number of "template" oligonucleotides which have to be synthesized are in the range of $n^2/2$, since one specific oligonucleotide has to be synthesized for each individual interaction on the library.

However, the present invention provides a method whereby the nucleic acid encoding the tags to identify both members of the interaction are formed upon joining of the two molecules. Hence, to investigate all interactions in a library of n members the number of oligonucleotides required is in the order of n. The combination of molecules in DTS is not combinatorial in the sense that all library members potentially may interact. It becomes combinatorial due to the presence of all specific pairs DNA templates which in turn direct the interactions. If the specificity of these interactions fails, the link between the compound phenotype and the nucleic acid genotype also fails. Thus, in the DTS approach, the link between nucleic acid identification tag and the molecules in the interaction depend on correct hybridization of one tag molecule to the template nucleic acid. If any cross hybridization occurs then the link between the tag and the identity of the interaction is unreliable.

In the current invention the nucleic acid formed by the NAM association encodes the combination of identification sequences. Therefore the link between the identification sequences in the associated nucleic acid molecule and the phenotype of the molecule is more effectively maintained.

The utilization of combinatorial association of different nucleic acid tags instead of pre-synthesis of all different combinations also provides further advantages. The amplification of the nucleic acid can be performed so that only nucleic acids which have been joined to create a pair of molecules are amplified by, e.g., introducing one primer site on each arm. Nucleic acids which remain unassociated will thus not be amplified. In the DTS approach all template nucleic acids can serve as PCR templates even though they have no interaction partner.

A method referred to as "proximity ligation" has been recently described (International Patent Application Ser. No. WO0161037, U.S. Patent Application Ser. No. US2002051986). According to this method, targets are detected by utilizing two or more binders, e.g. antibodies, with known affinity to the target. The method is based upon the co-localization of the binder pair in the presence of a target. This target brings the binders into proximity, enabling ligation of nucleic acids located on the binder pair. Thus the joining of the nucleic acid becomes elevated in the presence of the target molecule. The nucleic acid can subsequently be quantified and the amount of nucleic acid corresponds to the amount of target.

The primary embodiment of WO0161037 and US2002051986 aims at detection of a defined target. Thus all the affinities in the system are known and there is always at least one molecule, the target, which does not have a nucleic acid attached to it. Moreover, the invention utilizes two or more binders which bind their unlabelled analyte pair-wise in a predefined manner. Several pairs might be used in the same reaction but they are always analyzed in a target specific pair wise fashion, not in a combinatorial fashion.

The current inventive method differs from proximity ligation in that it does not detect or quantify a predefined target in a sample. The present inventive methods do not utilize molecules with predefined affinities but rather the reverse; the inter-molecular affinities are retrieved as a result of the inventive method.

In the current invention the association of the nucleic acid is combinatorial and the novel nucleic acid produced by this association is then identified to yield information concerning the molecular interactions in the library. This enables interrogation of all intra- or inter-library member interactions. The proximity ligation methods always include at least one molecule which is not attached to a nucleic acid label and this "target" is the molecule which is detected. Thus the co-localization/proximity of the binders and thereby the nucleic acid in the assay arises from the presence of a target molecule.

Finally the information gained from the inventions differs significantly. In the present inventive methods, combinations of interacting molecules may be detected and quantified. The proximity ligation art, on the other hand, teaches high throughput screening of inhibitors for a defined binding event. For example, a protein affinity interaction is identified first by some other method and proximity ligation is employed to find an inhibitor for the known affinity interaction. The proximity ligation screening approach involves attaching nucleic acids to the two proteins which participate in the predefined interaction. Then different potential inhibitors are added to the reaction. These potential inhibitors are not labelled with nucleic acids and their action is monitored by observation of a reduced signal from the two labelled proteins. The pre-defined affinity reagents are labelled with nucleic acids and a pre-defined pair of nucleic acids is analyzed.

There is a need in the art for methods capable of investigating affinity and/or functional interactions within libraries of molecules wherein such interactions are not previously established to exist, and methods for quantification of any detected interactions.

SUMMARY OF THE INVENTION

Accordingly, the present invention is directed to methods for discovering, as well as detecting molecular interaction networks such as affinity interactions or functional interactions, e.g., enzymes-substrate pairs. Significantly, the invention allows investigation of all possible interactions within or between libraries of molecules, such as proteins, and also permits relative quantification of the detected interactions. Information about the interactions is derived through the use of nucleic acid tags which facilitates high throughput analysis, preferably by microarray analysis, however other analysis platforms may also be used. Typically, each feature on the microarray corresponds to a molecular interaction between two specific molecules in the library.

Each molecule of interest (MOI) in the library is tagged with a nucleic acid tag, referred to herein as a nucleic acid moiety (NAM). If two molecules interact the combination of their nucleic acid tags is then selectively enhanced. The oligonucleotide formed from the combination of two NAMs is referred to herein as an associated oligonucleotide.

One embodiment is directed to a method of detecting an affinity interaction between at least two molecules of interest. The method comprises: (a) forming a plurality of interactors by coupling each molecule of interest with at least one nucleic acid moiety comprising an identification sequence element and at an association element; (b) promoting an association between at least two nucleic acid moieties to form a plurality of unique associated oligonucleotides, wherein each nucleic acid moiety may form more than one unique associated oligonucleotide, and wherein each unique associated oligonucleotide comprises at least two identification sequence elements derived from the at least two nucleic acid moieties; (c) selecting the plurality of associated oligonucleotides; and (d) subjecting the selected associated oligonucleotides to an analysis that permits detection of the at least two identification sequence elements.

According to this embodiment, an "interactor" library is developed. Each interactor consists of the molecule of interest (MOI) tagged with at least one unique nucleic acid moiety (NAM). The NAM comprises, inter alia, an identification sequence making downstream detection possible. It is the associated oligonucleotides which are subjected to qualitative and quantitative analysis, as a single associated oligonucleotide corresponds to an interaction between the two MOIs tagged with the NAMs that comprise that associated oligonucleotide. The library of interactors (NAM-tagged MOIs) is first allowed to interact and equilibrate. As the MOIs associate based on any affinity(s) between them, the corresponding NAMs associate in a proximity dependent manner incidental thereto.

Another embodiment of the present invention is directed to a method of detecting functional interactions between at least two molecules of interest. The method comprises: (a) forming a plurality of interactors by coupling each molecule of interest with a nucleic acid moiety, the nucleic acid moiety comprising an identification sequence element and an association element, wherein an affinity exists between the nucleic acid moieties; (b) forming a plurality of cis-reactive cells wherein a cis-reactive cell comprises at least two interactors bound in proximity to one another by an associated oligonucleotide formed from the affinity between at least two nucleic acid moieties, wherein the associated oligonucleotide comprises at least two identification elements derived from the at least two nucleic acid moieties; (c) subjecting the plurality of cis-reactive cells to conditions which stimulate a desired functional interaction having a detectable trace; (d) selecting all cis-reactive cells exhibiting the detectable trace; and (e) subjecting the associated oligonucleotides from the cis-reactive cells selected in (d) to an analysis that permits detection of the at least two identification sequence elements.

As in the affinity embodiment, each MOI is tagged with a unique NAM to form an interactor. However, in some functionality-based embodiments, the NAMs are designed to so that a pre-existing affinity exists between them. MOIs are independently tagged with the NAMs. Again, the interactor library is permitted to interact and equilibrate, creating a secondary library of "cis reactive cells" (CRCs) wherein each CRC consists of MOI molecules brought into proximity by the affinity between their respective NAMs, and co-localized by the association of their respective NAMs. Subsequently the function to be investigated is activated. When activated, MOIs will primarily act upon the other members in the CRC due to the proximity created by the physical linkage. In some embodiments it may be desirable to dilute the concentration of CRCs in order to lessen the probability of trans activation of the function. That is, activation between, rather than within, CRCs.

Following functional activation the secondary library is filtered for CRCs which contain MOIs that have been altered by the activation. Selection of positive (that is, altered) CRCs can be done by, e.g., affinity purification of the library of CRCs with respect to a modification introduced by an enzymatic reaction. The CRCs are then identified by the sequence motifs in the NAMs, thus both members of a functional interaction can be identified, for example, pairs of novel enzymes and novel substrates.

Schematic description of one embodiment for affinity interaction detection. A) Library morphology; a library with 1, 2, . . . , n MOIs, each associated with a defined NAM with nucleic acid tags 1, 2, . . . , n. B). The library is allowed to interact by affinity to induce co-localization of the MOIs and the respective NAMs. C) The association function of the NAMs is activated and NAMs brought into proximity by affinity between their respective MOIs are associated to for a novel associated oligonucleotide comprising nucleic acid from both of the originating NAMs. D) Selective amplification of the different NAM combinations. NAMs which are not associated will not yield any amplification product for subsequent detection.

FIG. 2

Schematic description of one embodiment for functional interaction detection. A) Library morphology; a library with 1, 2, ..., n species of MOI, each MOI species is associated with a defined NAM with nucleic acid tags 1, 2, ..., n. B) Construction of CRCs. The library association function is designed to co-localize the library members in a combinatorial fashion to create all possible CRC variants between the n library members ($(n-n^2)/2$ unique combinations). C) The functional interaction to be detected is activated and reaction conditions are controlled to restrict the functional interactions to substantially within the CRCs. D) Selection. Selection is carried out with respect to at least one detectable alteration introduced by the functional interaction. E) Amplification of the selected CRCs and subsequent detection and analysis of the nucleic acids.

FIG. 3

Schematic description of the library design in the exemplary approach described for affinity interaction. A) The NAMs are produced from a seed PCR product and unique NAMs are synthesized with tailed PCR primers comprising one of a plurality of nucleic acid tags. An association function is located in one primer and a conjugation function is located in the other. B) library morphology after conjugation to MOI. The association element in this case comprises a protruding end which allows selective blunt end ligation.

FIG. 4

Schematic description of the library design in the exemplary approach described for detecting a functional interaction. A) NAMs before conjugation to the MOI are depicted, including two separate sub-populations of NAMs comprising potential kinases and substrates respectively, one with the forward primer and one with the reverse primer. Each NAM comprises a PCR primer, identification element and an association element. B) Library morphology after association of the interactors to construct CRCs is illustrated. Each CRC is joined by addition of a polymerase that stabilizes the hybridization of the respective 3' ends and incorporates the nucleic acid tags and PCR primers into one associated oligonucleotide by polymerization.

FIG. 5

Figure 5:
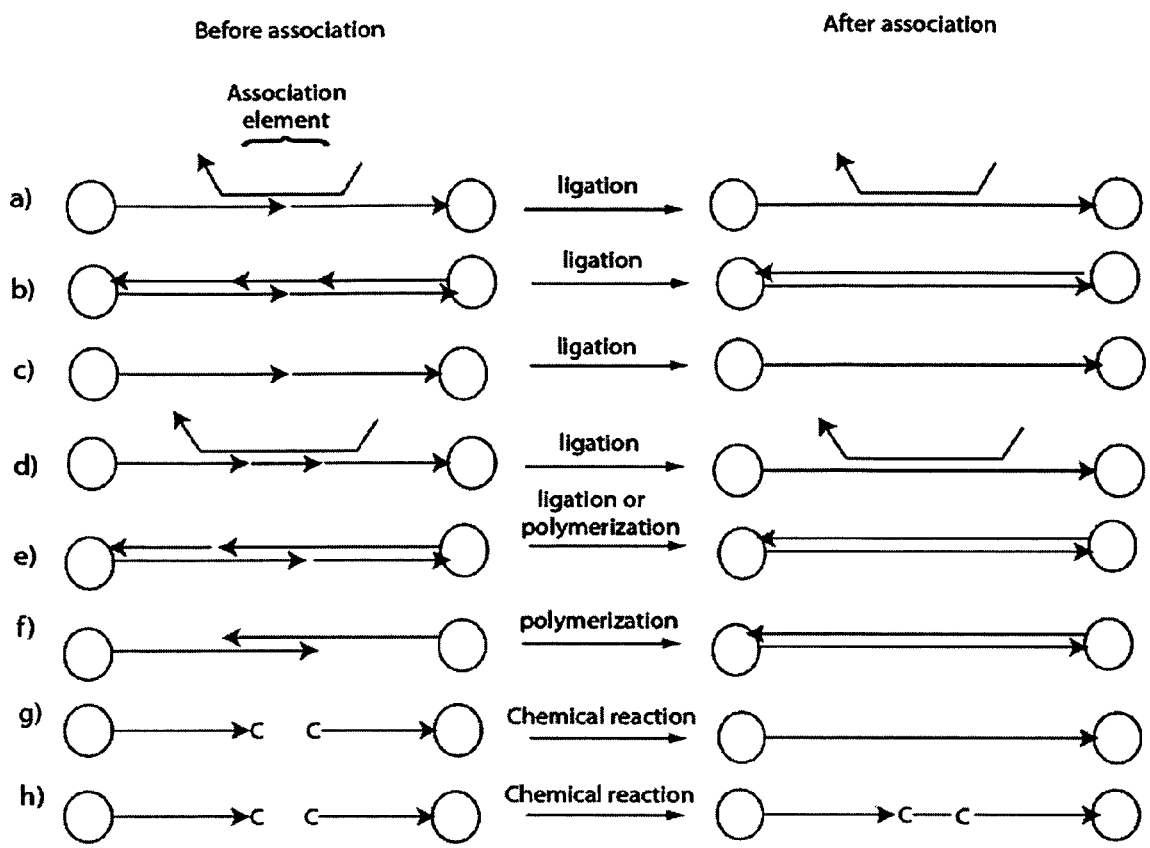

Non-limiting examples of association of NAMs. Arrows indicate nucleic acid 3' ends. FIGS. 5($a$-$d$) illustrate ligation approaches. The structure in 5($e$) can be associated with either ligation or polymerization with a polymerase comprising 5' exonuclease activity. 5($f$) can be associated with polymerization. 5($g$) illustrates association by introduction of a functional group which reacts to create a native nucleic acid. In 5($h$) reactive functions are used which associate the nucleic acids by a link separate from nucleic acid.

FIG. 6

Figure 6:
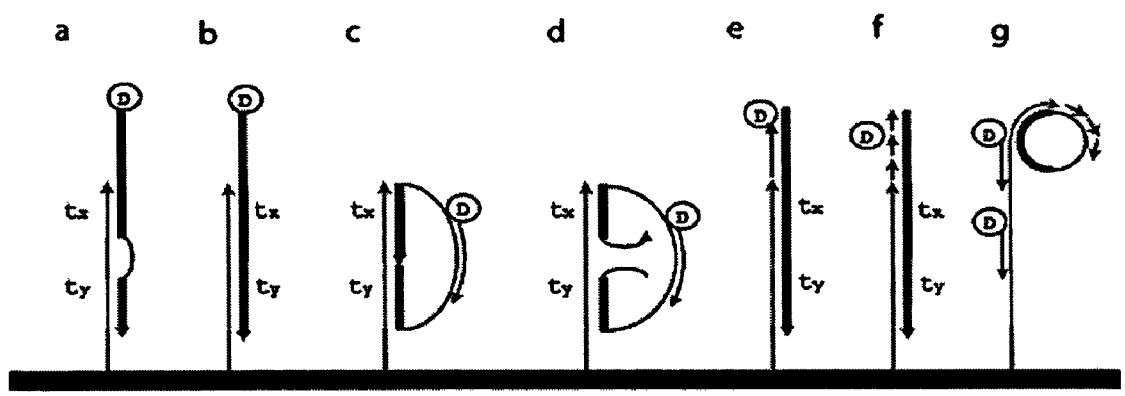

Examples of two tag microarray detection. Black sequences represent a general sequence common to all targets and red sequences represent identification tag sequences. 6($a$) illustrates hybridization of a target where the two tag elements are separated by a general sequence that is not complementary to the microarray probe. 6($b$) illustrates hybridization of a target comprising two identification elements not separated by any spacing or general sequence. In 6($c$) the identification tags are located in the 3' and 5' ends with the hybridized target forming a circular structure that could be ligation-templated by the microarray probe. In 6($d$) the target is hybridized to form a circular structure similar to 6($c$) but with a general spacing sequence at the ends of the target and in the microarray probe, an detection can be mediated by sandwich hybridization of a third nucleic acid or by direct labelling of the target. FIG. 6($e$) represents detection of a target with two joined tags by ligation of a third nucleic acid comprising a detectable function. In 6($f$) the detection is mediated by polymerization, for example, by a exonuclease deficient polymerase, rather than ligation. 6($g$) represents detection of the structure formed in 6($c$) by ligation of the circular structure, polymerization and subsequent detection by addition of a third labelled nucleic acid. The polymerization event could also be detected by labelled nucleotides.

FIG. 7

This represents results from the example for reaction discovery. Three tag microarrays from three experiments with different reaction conditions are displayed. A higher intensity represents detection of higher concentrations of the tag combination. Each hetero-interaction is represented by two separate microarray features.

FIG. 8

Figure 8:
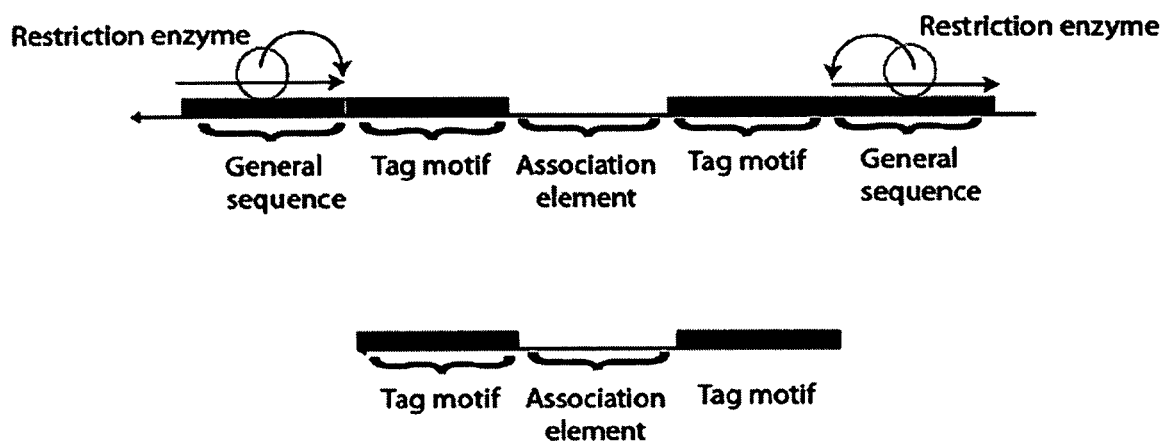

Illustration of a single stranded associated oligonucleotide or single stranded amplification product thereof. Two separate single stranded oligonucleotides comprising a type IIS restriction enzyme recognition sites are hybridized to the general sequence flanking the identification elements. The restriction enzyme cleavage occur between the identification element and the general sequence. FIG. 8($b$) Illustrates the single stranded DNA produced by the restriction enzyme cleavage with identification elements in the 3' and 5' end.

FIG. 9

Diagrammatic illustration of microarray features representing 3' arm and 5' arm tag combinations resulting from an interaction context. Data is plotted on a grid including the different 3' and 5' NAMs with the signal to noise (feature signal/sum of all feature signals) plotted on the z-axis. The arms with thiol groups are 3'A and 3'B and 5'C and 5'D.

DETAILED DESCRIPTION OF THE INVENTION

Terms & Definitions

As used herein, the term "combinatorial association" refers to association of a plurality of molecules to create a plurality of combinations of those molecules.

As used herein, the term nucleic acid moiety (NAM) refers to a nucleic acid molecule which is coupled to at least one molecule of interest (MOI). A NAM comprises at least one unique identification nucleic acid sequence so that detection of that sequence infers involvement of the coupled MOI. A NAM also comprises at least one element which enables association with other NAMs. A NAM may be single stranded DNA, double stranded DNA, single stranded RNA, double stranded RNA or combinations thereof. The NAM may contain modified nucleotides or nucleotide analogues. The NAM may be derived from synthetic, biochemical, biological synthesis or combinations thereof.

As used herein, the term "molecule of interest" (MOI) refers to a molecule about which interactive information is desired. An MOI is coupled with at least one NAM. In one embodiment each MOI is coupled with a single unique NAM. Examples of suitable MOIs include, but are not limited to, whole proteins, protein domains, peptides, peptoids, functional enzymes, low molecular weight compounds, small molecules, polymers, non-proteinaceous cellular products, virus particles, cells metabolites, lipids, carbohydrates, nucleic acids, inorganic compounds or combinations thereof. In one specific embodiment the MOI comprises proteins. In any library of MOIs, not all the MOIs may solely comprise nucleic acids. In a more specific embodiment, the MOIs may comprise factors regulating transcription, non-limiting examples include enhancers, repressors, and isolators) and DNA sequences. A library of such MOIs may be investigated for affinity interactions. In very specific embodiments the DNA sequences are derived from genomic sequences or comprise random elements. The DNA sequence MOIs may comprise genes involved in transcriptional regulation and the present inventive methods may be employed to reveal interactions between DNA and proteins to enable, for example, deduction of how the transcriptional units regulate transcription by binding to DNA.

As used herein, the term "small molecule" refers to a non-peptidic, non-oligomeric organic compound either synthesized in the laboratory or found in nature. Small molecules, as used herein, can refer to compounds that are similar to complex natural products which nature has selected through evolution, however, the term "small molecule" is not limited to these compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem. Soc. 1998, 120, 8565) and United States Patent Application 20030082830 "Synthesis of Combinatorial Libraries of Compounds Reminiscent of Natural Products", the entire contents of which are incorporated herein by reference.

As used herein, the term "interactor" refers to at least one MOI coupled with at least one NAM.

As used herein, the term "Cis Reactive Cell" (CRC) refers to an association of at least two interactor moieties, joined by an associated oligonucleotide. In a specific embodiment a CRC comprises two interactors.

As used herein, the term "interactor library" or "library of interactors" refers to a plurality of interactors.

As used herein, the term "Cis reactive cell library" or "library of cis reactive cells," or "secondary library" refers to a plurality of CRCs.

As used herein, the term "association of NAMs" refers to an association between the NAM components of interactors which results in a molecule containing nucleic acid sequences originating from the associated NAM molecules. This combination of NAMs is referred to herein as an "associated oligonucleotide" and, in specific embodiments, comprises the identification sequences for two component NAMs. The association may be covalent or non-covalent and occurs between at least two NAMs. In specific embodiments, the association occurs pairwise between two NAMs.

The types of interactions which may be detected with the current invention include, but are not limited to, interactions based on affinity, enzymatic activity including kinase, glycosylation, phosphatase and ubiqutinylation activity, fusion, covalent bond formation, structural alteration, degradation, and/or subunit addition. A person of ordinary skill in the art will recognize that an "affinity-based" interaction may include any interaction which results in non-random assortment of molecules due to any basis other than repulsion.

The current invention aims to retrieve information about molecular interactions. Interactions can be of any type between molecules such as e.g. affinity, enzymatic, structural, degrading, fusion, addition of one (or more) groups. The foundation of the interaction analysis is the increased probability of a reaction between molecules if they are brought in close proximity by molecular co-localization. The co-localized molecules will be prone to interact in cis rather then interact with separate molecules in trans with the presumption that the relative concentration of the co-localized molecules is higher then the concentration of other molecules in the solution. In the case of detection of affinity interactions the co-localization is introduced by the affinity interaction between the MOIs which then enhances the probability of the respective co-localized nucleic acids to associate. Functional interactions are detected by bringing the MOIs into proximity with one another through an independent assorting means. For example, MOIs may be brought into proximity with one another incidental to affinities between the NAMs, and then co-localized by association of the NAMs to form interactors. This increases the probability that all possible MOI groupings occur and are exposed to the functional trigger. A detectable function is then triggered.

The feature of intra-molecular enhancement of reaction kinetics frequently appears naturally in biological systems like, for example, transcription activation where affinities co-localize the transcription machinery to a gene initialized by binding of a transcription activator. The present inventive methods adapt such an approach in vitro as a molecular technique for analysis of molecular interactions.

According to the present inventive methods, interaction information is essentially encoded into nucleic acids which then are detected by nucleic acid analysis techniques. This is achieved by tagging each MOI with a NAM comprising a unique nucleic acid identification sequence. (In some embodiments more than one MOI may be tagged with the same NAM species). The downstream association of NAMs form a novel oligonucleotide molecule encoding the interaction. This approach allows combinatorial analysis of all potential interactions in a library if all different tag combinations can occur.

The following detailed description of the Interactor Library is divided into the following sections for clarity: components; construction; interaction analysis; filtering; and readout.

Interactor Library

Library Components

The current invention is based upon the construction of a library of molecules referred to herein as interactors. These library members comprise at least two distinct parts which are coupled, one part is the molecule of interest (MOI) and one part is the nucleic acid moiety (NAM).

Molecule of Interest (MOI)

The MOI component comprises molecules including, but not limited to, whole proteins, protein domains, functional enzymes, low molecular weight compounds, polymers, non proteinaceous cellular products, virus particles, cells metabolites, lipids, carbohydrates, nucleic acids or combinations thereof. The library may consist of a heterogeneous population of MOI types. Minimally, the MOI component must meet two requirements, it must be coupled with at least one uniquely identifiable NAM, and not all MOIs in the library can be nucleic acids.

Nucleic Acid Moiety (NAM)

The NAM may comprise single stranded DNA (ssDNA), double stranded DNA (dsDNA) single stranded RNA, double stranded RNA or combinations thereof. It may include any type of modified nucleotides or nucleotide analogues or other types of molecules which can be incorporated into nucleic acids. The coupling between a NAM and an MOI to form one interactor may be non covalent but covalent association is desirable. Each NAM is coupled to at least one MOI and it may associate with other NAMs in the library.

Interactors

One interactor in the library comprises at least one MOI coupled to at least one identifiable NAM. The inventive methods enable retrieval of information concerning interactions between these interactors in vitro. The retrieved data can then be translated into information about the interactions of the MOIs.

Library Construction/Coupling of MOI and NAM

The inventive methods prepare and utilize libraries of interactors as described above. These libraries can be synthesized in several different ways. The construction of the interactor library includes coupling of at least one MOI to at least one NAM. Generally the coupling means may be specific or unspecific with respect to coupling position and couplings may be performed in trans and cis. In other embodiments an interactor comprises more than one MOI and at least one NAM.

Coupling of MOIs and NAMs in Trans

It is possible to construct an interactor library merely by mixing a plurality of MOIs with a plurality of NAMs and permitting them to incubate and couple under conditions that favor coupling. Possible mechanisms of coupling include, but are not limited to, chemical, enzymatic or affinity based mechanisms. Preferably the coupling between the MOI and the NAM is covalent and stable or at least of high affinity. The coupling of the MOI to the NAM may also include addition of one or several types of bi-functional linkers. The coupling may be specific or nonspecific.

Nonspecific coupling includes means wherein the exact position of the NAM might not be controlled or known and wherein several NAMs might couple to one MOI. However, unspecific coupling of the NAM to the MOI might interfere with or alter the interaction phenotype of the MOI. Therefore specific coupling may be desirable when possible. Specific coupling includes methods where the position of the NAM on the MOI is controlled and/or known. To control localization of the NAM a reactive functionality may be introduced on the MOI during or after synthesis of the molecule, whether synthesis is chemical, enzymatical, in vitro or in vivo. This will secure NAM coupling with the MOI at defined position(s) on the MOI. Depending on the nature of the MOI, specific coupling of the NAM may be performed downstream of MOI synthesis without modification of the MOI if there is a novel site(s) on the MOI to which the coupling can be directed.

Examples of Specific Coupling Means

Generally, specific coupling may be accomplished by introduction or utilization of a site(s) on the MOI to which a specific coupling can be directed. The site can be used for direct coupling of the NAM or coupling to a third molecule which then can be coupled with the NAM. The nature of the association can be of covalent or non covalent as long as the link between the MOI and the NAM is maintained. Different interactors in the library may be produced with different approaches for association of the respective MOI and NAM molecules depending on the nature of the interactor.

One example of a specific coupling means is the generation of a specific site by intein splicing. Several examples of this which may be utilized in the present inventive methods are disclosed in Takeda et al. *Bioorg Med Chem Lett* 14, 2407-2410 (2004), Southworth, et al. Biotechniques 27, 110-114, 116, 118-120 (1999), and Burbulis et al. "*Using Protein-DNA Chimeras to Detect and count small numbers of molecules*" 2, 31-37 (2005), all of which are incorporated fully herein by this reference. Generally, this approach creates a site for specific chemical conjugation in either the N-terminal or the C-terminal of a protein. An intein approach which could be used for both MOI purification and conjugation has been commercialized by New England Biolabs under the trademark IMPACT-TWIN. Specific coupling of the NAM to the MOI may also be performed by introduction of a fusion partner to the MOI which has affinity or enzymatic activity towards the NAM or vice versa. A specific example of this is the introduction of the hAGT protein as a fusion partner to the MOI and addition of the hAGT substrate to the NAM. hAGT then covalently binds the substrate on the NAM. This has been used to conjugate different molecules to proteins fused to hAGT as disclosed in Keppler et al. *Methods*, 32, 437-444 (2004), also incorporated fully herein by this reference.

A specific site may be introduced on the MOI to which a function for coupling then can be introduced downstream of synthesis. An example of this approach is the utilization of biotin ligase as taught in Duffy et al. Analytical Biochemistry 262, 122-128 (1998), the disclosure of which is fully incorporated herein by this reference. Briefly, a signal peptide is incorporated into the MOI during synthesis, which then is recognized by the biotin ligase. The biotin ligase recognizes the peptide and adds a biotin to the MOI. This biotin can then be used for coupling of the NAM by introducing an affinity molecule such as streptavidine or avidine on the NAM. The introduction of the biotin may be performed in vitro or in vivo.

Examples of Unspecific Coupling Means

Unspecific coupling includes the use of chemical coupling to sites on the MOI which yield a coupling between the NAM and the MOI where the exact position of each NAM is uncertain and where the coupling may occur to several different sites on the MOI. These approaches would typically include one reagent (A) which can couple to the NAM and one reagent (B) which can couple to the MOI and a subsequent step where A and B are associated. There is also the possibility to associate A and B first or utilize a molecule which binds both the NAM and the MOI. A person of ordinary skill in the art will appreciate that the diversity of these molecules is quite high and the choice will depend upon the nature of the MOI. Specific nonlimiting examples of functional groups which can be used for this type of coupling include NHS esther, malemide, Azide, Alkyne, amine, or thiol. For more examples see; Double-Agents Cross-Linking Guide (#1600918) from Pierce. Coupling can also be mediated by a reactive group on the NAM which reacts directly with the MOI or vice versa.

Coupling Between MOIs and NAMs in Cis

Instead of individual construction of the library interactors, the coupling between the NAM and the MOI can be performed during the synthesis of the MOI. The synthesis is controlled so that it will produce coupling with at least one defined NAM. The interactor synthesis can be performed in multiplex, i.e. several interactors can be synthesized in the same reaction. This could potentially speed up the library construction significantly.

Nonlimiting examples of this include the approach used in CIS display or Covalent display as disclosed by Reiersen et al. Nucleic Acids Res 33, e10 (2005), or Odegrip, R. et al *PNAS* 101, 2806-2810 (2004), the disclosures of which are fully incorporated herein by this reference. A library of proteins is produced and during production the protein product is specifically associated to its own DNA by a protein fusion partner. Variants of this approach have been published whereby the coupling is covalent or non covalent. In a modified approach this could be used to create libraries where the protein serves as the MOI and the thereto coupled DNA molecule serves as a NAM.

Another approach is the use of the mRNA display technique disclosed in Wilson et al. PNAS 98, 3750-3755 (2001), fully incorporated herein by this reference. According to this approach a pool of proteins is produced from a pool of mRNA templates and the protein products are coupled with the mRNA they were produced from by a pyromycin modification at the end of the mRNA. The protein then serves as the MOI and the coupled mRNA as the NAM. A modified variant of this exists where the protein product is linked to a cDNA instead of the mRNA.

Another approach which creates a physical link between the RNA and the protein is ribosome display, taught by Hanes & Pluckthun in PNAS 94, 4937-4942 (1997), the disclosure of which is fully incorporated herein by this reference. However in this particular coupling technique, coupling is mediated by the ribosome which is a large complex with the potential to interfere with the assay. The design of the coupled nucleic acid could be adapted to the current invention in these systems and the nucleic acid component may be modified post synthesis by, e.g., restriction endonucleases. In the genetic protein based systems the nucleic acid sequence encoding the proteins could be utilized as the nucleic acid identifying sequence for downstream detection. Constant sequences present on all nucleic acids in the library could be utilized for amplification.

A person of ordinary skill in the art will appreciate that any method which utilizes a function which couples the DNA or RNA with the protein product during synthesis could fulfil the purpose of creating libraries of interactors in multiplex employable herein. This has the additional advantage of ensuring integrity between the genotype and the resultant phenotype in display techniques. The important feature in these approaches is that the coupling between the nucleic acid and the MOI occurs in cis. Thus, the binding of the nucleic acid primarily occurs to the protein product synthesized from that nucleic acid. For coupling between DNA and protein this is mediated by the fact that the DNA is attached to the protein product by the transcription and translation machinery.

The desired MOI-NAM coupling may be achieved by a variety of means including fusion of MOIs to nucleic acid binding proteins which bind back to the nucleic acid upon synthesis and addition of molecules to the RNA or DNA which bind the synthesized protein or an attached fusion partner. The binding may be directly or indirectly mediated by a bifunctional linker, that is, an intermediate molecule holding the DNA and protein together. This intermediate molecule may range in size from a small molecule as defined herein, to a very large ribosome. The cis coupling of a nucleic acid to a desired protein could also be mediated by in vivo expression of, for example, plasmids, phages or viruses. If the nucleic acid encoding the protein product is utilized as the NAM, constant motifs can be used for amplification purposes and MOI encoding motifs for identification. One specific embodiment of the present invention is directed to methods of detecting affinity interactions between at least two molecules of interest, wherein at least one molecule of interest comprise a protein that is an expression product of a nucleic acid molecule, and wherein at least some of the plurality of interactors is formed by coupling the protein with a nucleic acid moiety comprising an identification sequence element and an association element derived from the nucleic acid molecule. This provides a library of interactors wherein each interactor comprises a molecule of interest comprising a protein that is an expression product of a nucleic acid molecule, coupled with a nucleic acid moiety tag, the tag comprising an association element and an identification sequence element, wherein the identification sequence element and the association element derived from the nucleic acid molecule.

DTS, described in Kanan et. al *Nature* 431, 545-9, herein incorporated fully by this reference, permits multiplex synthesis of MOIs other than proteins. DTS may be utilized to synthesize libraries encoded by nucleic acids and these library members can subsequently be utilized as interactors in the current invention.

Interaction Analysis

The present invention provides methods which permit analysis of the interactor library with respect to interactions between the interactor members, and, therefore, by inference, between the MOIs. One embodiment provides analysis based primarily on affinity interactions between the MOIs. Another embodiment provides analysis based primarily on functionally-based interaction between MOIs. Affinity interactions are interactions where two or more members of the library display a binding affinity towards each other. Functional interactions are interactions where two or more members affect each other in some detectable way and may include affinity interactions, though a person of ordinary skill in the art will appreciate that there are functional interactions which display very low or transient affinity.

Affinity Interactions

One embodiment of the present invention is directed to a method of detecting an affinity interaction between at least two molecules of interest. The method comprises: (a) forming a plurality of interactors by coupling each molecule of interest with at least one nucleic acid moiety comprising an identification sequence element and at an association element; (b) promoting an association between at least two nucleic acid moieties from different interactors to form a plurality of unique associated oligonucleotides, wherein each nucleic acid moiety may form more than one unique associated oligonucleotide, and wherein each unique associated oligonucleotide comprises at least two identification sequence elements derived from the at least two nucleic acid moieties; (c) selecting the plurality of associated oligonucleotides; and (d) subjecting the selected associated oligonucleotides to an analysis that permits detection of the at least two identification sequence elements.

Broadly, affinity interactions are defined as interactions between two or more molecules that induce a non-random distribution of these molecules in a solution comprising these molecules. Thus, the molecules which display the affinity will more frequently be close to each other then if their distribution were random. It is noted in particular that a non-random distribution per se may be due to a repulsion between the MOIs such that the MOIs are more frequently separated than in a random distribution.

Affinity interactions within the interactor library are analyzed by allowing the library members to mix and equilibrate under conditions which permit affinity interactions. Following this step association of NAMs is actively promoted. The association of NAMs is performed so that association between two NAMs depends on proximity of the NAMs, with the proximity being due to an affinity interaction between their respective MOIs. Thus MOI affinity interaction induced proximity or co-localization of NAMs induces a higher association frequency of those NAMs compared to a control where the MOI affinity is absent. Downstream of the association, the associated NAMs (the associated oligonucleotide) can optionally be amplified and subsequently detected, by, for example, microarray analysis.

A person of ordinary skill in the art will recognize that a stronger affinity between two MOIs generally induces more frequent association of the NAMs. This enables a relative quantification of the interaction affinity strength between interactors and, by inference, the MOIs.

Functional Interactions

Another embodiment of the present invention is directed to a method of detecting functional interactions between at least two molecules of interest. The method comprises: (a) forming a plurality of interactors by coupling each molecule of interest with a nucleic acid moiety, the nucleic acid moiety comprising an identification sequence element and an association element, wherein an affinity exists between the nucleic acid moieties; (b) forming a plurality of cis-reactive cells wherein a cis-reactive cell comprises at least two interactors bound in proximity to one another by an associated oligonucleotide formed from the affinity between at least two nucleic acid moieties, wherein the associated oligonucleotide comprises at least two identification elements derived from the at least two nucleic acid moieties; (c) subjecting the plurality of cis-reactive cells to conditions which stimulate a desired functional interaction having a detectable trace; (d) selecting all cis-reactive cells exhibiting the detectable trace; and (e) subjecting the associated oligonucleotides from the cis-reactive cells selected in (d) to an analysis that permits detection of the at least two identification sequence elements.

Functional interactions are defined as interactions between molecules where the nature of at least one of the partners which participate in the interaction deviates from the nature of that partner when the other participant(s) of the functional interaction is/are present in conditions permitting the functional interaction. Functional interactions may include an affinity interaction.

Functional interactions include interactions with functions such as, e.g., kinase, phosphatase, glycosylation, deglycosylation, ubiqutinylation, deubiqutinylation or other paired activities where one member adds or removes a molecule(s) from the other member. Additional nonlimiting examples include interactions with altering activities such as cleavage, fusion, and inducement of a structural alteration in one or more members of the interaction. Significantly and advantageously, the present invention permits identification of both partners of a functional interaction. The criterion for detection of functional interactions by this approach is that the functional interaction is capable of being detected or selectively enhanced to permit detection.

The approach to identify functional interactions is similar to that for identification of affinity interactions but differs in some key features. When employing the previously discussed embodiment directed to affinity interactions, the association function of the NAMs is activated after interactors are permitted to display any affinity interactions which may detectably exist. In the case of detecting functional interactions the MOI association activity is controlled and the interactors in the library are forced together by association of their respective NAMs, NOT primarily between any affinities between the MOIs. One way to achieve this is by introducing an affinity between the different NAMs in the library by hybridization. This will create co-localizations of two or more interactors through the association of the NAMs. The result of the forced NAM association is a secondary library of cis reactive cells (CRCs). A CRC is a co-localization of two or more interactors which are associated by their NAMs (associated oligonucleotide). Thus the MOI components of the same CRC are brought in proximity although the MOIs might not have any intrinsic affinity. However, it is contemplated that in some embodiments the CRCs may be created by relying on intrinsic MOI affinities or a combination of both MOI affinity and NAM affinity.

If two individual MOIs are members of a functional interaction pair and the conditions favour this function, the MOIs in one CRC, being in closer proximity to one another, will interact more frequently with one another than with MOIs in other CRCs. It is important that the interactor concentration in the library be maintained lower than the relative concentration between the MOIs in the CRC.

Once the CRC library is constructed the functional interaction being investigated is stimulated. This can be accomplished by, for example, addition of a substrate or a shift in reaction conditions. The MOIs in the CRC will primarily act on each other in cis since they are physically linked, but they could potentially act in trans with MOIs in other CRCs. Hence, measures are taken to ensure that any functional interactions remain substantially restricted within the CRCs. Such measures may include, but are not limited to: temporal limitation of the functional activity; competition with the reverse functionality; and dilution of the associated library.

In one specific embodiment, temporal limitation of the functional interaction is achieved by adding a component essential for the activation in a milieu where this compound is rapidly degraded. The degradation of the component may be chemical or enzymatic. In a further specific embodiment, competitive limitation is achieved by activating the functional interaction in a milieu where it is reversed. The action which reverses the functional interaction could be of chemical or enzymatic nature. If the functional interaction includes addition of a molecular group or alteration of a structure the reaction conditions can be maintained so that the added group hydrolyses or the structure reverts to the initial state quickly. Employing enzymes which remove the group added by the functional interaction may also be an option. If a functional interaction is present within a CRC it might be counteracted by the reaction conditions or by the addition of compounds but the intrinsic functional activity of the CRC will immediately counteract this. On the other hand, if a member of a CRC acts in trans on a separate CRC this functional interaction will be reversed by the reaction conditions and the probability of a repeated functional interaction in trans is low. Thus, an equilibrium that favour functional interactions within CRCs can be achieved.

In another specific embodiment, the CRC library is diluted subsequent to association of the interactors but prior to activation of the function being investigated. Interactor association will be more efficient at higher concentrations, but this also elevates the risk of trans interactions between the CRCs once the function is triggered. Diluting the concentration after formation of the CRCs will lower the concentrations of CRCs in the library while the proximity between MOIs within the CRCs remains.

The library is then analyzed with respect to which CRCs display the desired functional interactions. The functional interaction being investigated is limited to those functions that are detectable.

Association of NAM Molecules

Association of interactors is a key feature of the current invention in both the embodiment for detection of affinity interactions and the embodiment for detection of functional interactions. The binding of the interactors by their respective NAM association elements forms novel molecules, herein referred to as associated oligonucleotides, comprised of the nucleic acid tags comprising the identification sequences derived from the component interactors. Analysis of the associated oligonucleotide molecule formed from the combination of these tags permits identification of the interactor MOI components.

It is desirable that the NAM association results in a molecule comprising nucleic acid derived from each of the associated interactors. There are several approaches to achieve this and the examples described below and in FIG. 5 serve to illustrate some approaches, though this should not be construed as excluding other approaches. Association by enzymatic ligation may be achieved as illustrated in FIGS. 5(a-e). Ligation substrates may include single stranded nucleic acid templated by a third nucleic acid, double stranded nucleic acid with protruding ends templated by a third nucleic acid, ligation of single stranded nucleic acids, templated ligation where a separate nucleic acid is introduced into the ligation product or ligation of double stranded nucleic acid with complementary protruding ends. Exemplary association approaches for polymerization include substrates comprising double stranded nucleic acid with complementary protruding 3' ends, or single stranded nucleic acid with complementary 3' ends, as illustrated in FIGS. 5(d) and 5(f).

Association may also be accomplished via chemical rather than enzymatic ligation. Chemical ligation may be performed by providing nucleic acids with reactive groups on the ends which allow association by chemical reaction. The chemical reaction may result in a nucleic acid of native composition which can serve as, for example, a polymerization substrate, or a nucleic acid derivative which does not serve as polymerization substrate. Two illustrative approaches for chemical association are illustrated in FIGS. 5(g) and (h). Other non-limiting examples of NAM association approaches which could be used are gap fill polymerization and subsequent ligation and gap ligation as described in Lizardi et al. *Nat Genet* 19, 225, 232 (1998), or invader cleavage and subsequent ligation as described in Lyamichev et al, *Science* 260, 778-783 (1993), both of which are fully incorporated herein by reference. In a specific embodiment the nucleic acid is DNA but other nucleic acids may also be used.

The association approach utilized depends on the qualitative assay design. An illustrative example is the introduction of PCR amplification. If PCR amplification of associated NAMs is desired the association may preferentially combine NAMs comprising the forward primer with NAMs comprising the reverse primer to form amplification substrates. Selective association may be achieved by introduction of the forward primer to a portion of the interactor library with the association element in the 3' end and the reverse primer in another portion of the interactor library with the association element in the 5' end. This would be desirable since both primer motifs are required for amplification of associated NAMs by PCR.

In one embodiment, selective association approaches which exclude homo-association permit construction of interactor libraries with interactors comprised of more then one NAM per MOI. If homo-association is not excluded, then the homo-associations of NAMs associated to the same MOI be very efficient and potentially render the library useless.

In one embodiment, two sub type libraries are constructed wherein each subtype comprises a different NAM and the NAMs of one subtype can associate only with NAMs from the other subtype. If the associated library is enhanced with PCR subsequent to association each NAM sub type comprises one of the PCR primer motifs. In the case of affinity interactions this design also allows association of several NAMs to each MOI, since unique NAMs are unable to associate. For functional interactions, the design allow presentation of all possible interactor combination in one mixing step, such as when interactor libraries comprising different NAM subtypes are pooled. If the NAM association is efficient and/or of high affinity this has the potential to override affinities present between MOIs since each interactor will associate with any interactor comprising a compatible NAM and this may occur before equilibrium is achieved with respect to the individual MOI affinities. Subsequent to construction of CRCs, the interactor library can be diluted to reduce the effects of MOI affinities between CRCs.

Association of Nucleic Acids in for Affinity Interaction Analysis

For investigation of affinity interactions it is desirable to use NAMs comprising ssDNA or dsDNA. For investigation of affinity interactions it is important that the different NAMs do not display too high of an intrinsic affinity toward one another other. The affinity between the different association elements of the examples illustrated in FIGS. 5(a) to (f) depend on the length of the complementary sequences of the association elements, and the addition of a third nucleic acid where applicable, except in 5(c) where no complementary sequence is present. Low affinity may by achieved by restricting each complementary sequence to 1-10 nucleotides. Association of NAMs by addition of a third templating nucleic acid can advantageously be performed by template addition in high concentration (e.g. >100 fold) compared to the interactor concentration. This will provide template mediated association of NAMs proximal at the moment of addition, while individual NAMs will hybridize to templates individually. Once all NAMs have hybridized to a template nucleic acid, this hybridization can block further template mediated dimerization of NAMs by intrinsic stability. This approach may allow utilization of template nucleic acids with higher stability.

Association of Nucleic Acids for Functional Interaction Analysis

CRCs are constructed by the association of NAMs. The association may advantageously force different MOIs together and therefore affinity between the different NAMs is desired. In the exemplary illustrations 5(a, b, d, and f) this is achieved by introducing stable complementary sequences in the association elements.

When a third templating nucleic acid is employed for construction of CRCs, this may advantageously be added in equimolar or slightly higher (e.g. <5 fold excess) concentrations compared to the total interactor concentration. This may introduce an equilibrium where a majority of the NAMs are associated.

According to another embodiment, association between NAMs with low intrinsic NAM affinity is employed to construct a CRC library wherein the frequency of each CRC depends on the relative affinities of the interactors. This permits investigation of both affinity interactions and functional interactions with the same library. The CRC library may also be enriched for CRCs subsequent to association to avoid trans-interactions from individual interactors.

The association reaction can also be regulated by reaction conditions. For example, in an exemplary library comprised of proteins the protein-protein affinity interactions may be destabilized by introduction of high salt concentrations, which also stabilizes the nucleic acid interactions. Thus the inter-interactor affinities are shifted to depend on the nucleic acids.

Filtering and Selection

Affinity Interactions

The selection in the affinity embodiment of the inventive methods primarily concerns elimination of interactors which are not associated with any other interactors and maintaining the associated interactors. This can be achieved in several ways. One way is to perform selective amplification of associated NAMs, for example, with PCR, wherein there is one primer on each NAM so that only joined NAMs will produce amplification products. This approach might necessitate two types of NAMs per MOI (one with each primer motif) to enable identification of all interactions in the library including homo interactions.

A second amplification-based selection method is to cut the respective arms with a restriction enzyme and circularize the nucleic acid with a general template. Upon a second ligation, ligated arms will form a circular structure while individual arms will form a linear structure. The circular nucleic acid can then selectively be amplified by rolling circle amplification, a well-known technique in the art. Another way is to immobilize one part of the library to a solid phase and then perform the association of the NAMs. After the association, washing may remove all interactors which have not associated with any immobilized interactors. All molecules may or may not be present in solution or immobilised on the solid phase. The interactors may be immobilized in a spatially organized way or in a random fashion. Following washing of the solid phase the combinations of NAMs may be analyzed with or without amplification. One example of a suitable procedure would be elution of the interactors and amplification of the associated NAMs.

According to another embodiment, associated NAMs are selected by degrading any NAMs which are not associated. An example of this approach would be addition of an exonuclease which degrades any free nucleic acid ends. If the NAMs have been associated with a ligase the associated NAMs will not have any free 5' or 3' ends and not be amenable to degradation.

Functional Interactions

To detect functional interactions in a pool of CRCs the CRCs which display functional interactions must be selected for detection and/or analysis. It will be appreciated by one of ordinary skill in the art that this step will be modified according to the nature of the functional interaction that is being investigated. As used herein, a "filter" or a "filtering process" is the means employed to selectively separate the desired CRCs. Nonlimiting examples of filters for functional interactions include: affinity purification of the form which has undergone alteration in the functional interaction; detection of the CRCs by labelling with affinity reagents which detect interactors which are included in the functional interaction; and introduction of a modified molecule which becomes incorporated by the functional interaction where the modification permits selective detection. Downstream of the filtering process of CRCs the compositions of associated NAMs are detected and/or quantified.

One example of a suitable filtering process is, affinity purification. Filtering of positive CRCs in the case of an interaction which includes addition of a group by one member of the interaction to the other member such as a kinase or a glycosylation interaction between enzyme and substrate may be accomplished by affinity purification of CRCs with respect to the added group. In the specific example of a kinase interaction the library of CRCs can be affinity purified with a phosphate specific antibody. The specificity can be controlled to a phosphorylated amino acid, peptide motif or a whole protein depending on the assay. CRCs which do not contain the modification will be discarded and the CRCs with a modification will be retained and detected. Each CRC with a modification can be assumed to contain two members with the activity screened for, unless a homo interaction occurs. So in the case of kinase activity each selected CRC contains one kinase and one substrate thereof. The affinity filtering could also serve as a negative selector where the undesired molecules remain on the solid phase and the desired ones are collected. As non-limiting examples, this type of selection would be suitable in the case of phosphatase activity, glycosylation/deglycosylation, ubiquitinylation/deubiquitinylation and for any other interaction which serves to add or remove molecules or parts from one of the interaction partners as long as there are a specific affinity reagent for the molecule or part which is added or removed.

If the functional interaction results in a structural change in one of the partners to the interaction, affinity purification can be performed which only recognizes the altered portion. If no affinity reagents are available for the molecule which is added or removed an affinity function could be attached to the group which is added. For example, a protein like ubiquitin may be fused with one interaction partner and the added ubiquitin may be labelled with biotin which may then be affinity purified with streptavidine. However the "filtering" is not necessarily through affinity purification and can also be, for example, a conditional detection of the NAMs. If the detection output is coupled to the result of the interaction, for example, with an affinity reagent for the modification, only the CRCs with positive interaction pairs will be detected.

Another example of a suitable filtering process is conditional detection. The CRCs can be hybridized to a DNA oligonucleotide tag array where all possible combinations of identification sequences in the library are present. The different combinations of associated NAMs are spatially separated by the hybridization. To identify which NAM combinations represent a CRC with a positive interaction pair the array with the CRCs can be stained with a labelled affinity reagent specific for the interaction. However this approach requires that the MOIs are present during detection and thus no amplification of the associated NAMs is possible. A detectable function may also be associated with a modification, more specifically, for example, a fluorescent or radioactive label can be introduced by the modification, which more specifically comprises, in kinase interactions for example, a radioactive phosphate group.

Detection

In one embodiment, detection or readout of the library interactions is achieved by analysis of the NAM combinations, both qualitatively and quantitatively, by nucleic acid analysis. In a more specific embodiment, the nucleic acid composition is analyzed using microarrays. Other embodiments contemplate other known and unknown methods of nucleic acid analysis or include detection of molecules attached to the NAMs or the respective MOIs. The important feature is that at least two bits of information are retrieved, each representing one partner of the interaction.

Nucleic Acid Based Readout

In one specific example, the analysis of interactions present in the library is accomplished by analysis of the combinations of the NAM elements by microarray analysis. The analysis of the associated oligonucleotides is similar both for the affinity interaction assay and functional interaction assay, once the CRCs of the functional interaction assay are filtered/selected for those CRCs which contain functionally positive interactors as described above. In some embodiments, the detection of the associated oligonucleotides is preceded by an optional amplification step.

Amplification Methods

To increase the sensitivity and speed up the analysis, the associated oligonucleotides can be amplified by conventional nucleic acid amplification techniques such as, for example, polymerase chain reaction (PCR), rolling circle amplification (RCA), strand displacement amplification (SDA), nucleic acid sequence based amplification (NASBA), RNA transcription or invader assay. If the NAMs comprise RNA, reverse transcription may be used to translate these sequences into DNA. Other embodiments contemplate additional methods, known and unknown, of nucleic acid amplification. In the case of affinity interactions the amplification can also be used as a step to select for associated NAMs.

When PCR is utilized for amplification of associated NAMs, two primer motifs are required. In one specific example, PCR is used for amplification of associated NAMs wherein one primer motif is located on each NAM so that associated NAMs are selectively amplified. However PCR amplification requires two types of NAMs per MOI, one for each respective primer, to enable amplification of all intra-library MOI combinations. If inter-library interactions are detected, the libraries can be designed to comprise separate primer motifs.

RCA amplification of associated NAMs requires synthesis of a circular polymerization substrate. Conversion of the associated oligonucleotide constructed upon NAM association to a circular substrate can be achieved by removing the MOIs by, for example, restriction enzyme digestion and allowing circularization of the associated oligonucleotide by templated intramolecular ligation.

Sequence Information Retrieval Approaches

The pertinent information which must be retrieved from the associated oligonucleotides is the identity of the two identity sequence motifs which provide information about the identity of the MOIs corresponding to that associated oligonucleotide. Thus at least two pieces of information need to be decoded. There are several ways to do this and most of them are either sequencing based or hybridization based approaches.

Hybridization Based Approaches:

The use of microarrays to identify nucleic acid sequences in complex pools is well-known and has been adapted to high throughput platforms, for example, in expression profiling. The utilization of oligonucleotide arrays has increased the specificity and the introduction of in situ oligonucleotide synthesis has enabled very high throughput analysis by cheap probe synthesis of very complex microarrays. Currently the major platforms for microarray hybridization to oligonucleotides are fabricated by either robotic deposition of chemically synthesized oligonucleotides or in situ synthesis of the oligonucleotides on the array. Separate platforms for microarray readout also exist, such as the Illumina platform, wherein oligonucleotides are attached to beads which subsequently organize on a solid support by self assembly.

The present inventive methods detect different tag combinations. If a library consists of n different interactors, each with a different identification sequence in the NAM, there would be $(n+n^2)/2$ potential combinations including homo-interactions, and $(n^2-n)/2$ potential combinations without homo-interactions. If two subtypes of NAMs are utilized for one MOI library, each subtype with a unique set of identification sequences, the number of tag combinations will be $n^2$, where each interaction is represented by two separate unique tag combinations except the homo-interactions.

Microarrays with probes for all these nucleic acid tag combinations could be manufactured for readout. The number of probes needed increase exponentially with the number of library members according to the formula above. However in situ synthesis of microarrays can produce very complex arrays which could be used for any interaction study since the nucleic acid tag set generally is independent of the MOIs.

The general approach to detecting the NAM combinations by microarray based readout involves construction of a microarray wherein all possible tag combinations in the library are present. The associated oligonucleotides, or amplification products thereof, are allowed to hybridize to the array. Preferably the melting temperature of the identity sequence elements should be designed so that the difference between hybridization of one element and two elements is maximized. Other criteria that increase hybridization stringency could also be introduced to maximize specificity, such as, for example, enzymatic discrimination steps. Non-limiting examples of these include ligation and/or polymerization.

The design of the microarray-based dual tag detection includes hybridization of a nucleic acid comprising at least two separate tag or identification sequence motifs to array probes with their respective complements. Illustrative examples of microarray hybridization designs are provided in FIG. 6. Hybridization of the two identification sequence elements $t_x$ and $t_y$ (red in FIG. 6) may be accomplished by hybridization with or without a general sequence (black in FIG. 6) present on the targets. The elements may be hybridized as a continuous sequence (6b) or with a spacing sequence between the elements (FIG. 6a). The elements may also be designed to form a circular structure upon hybridization (FIGS. 6c and d). The specificity of the detection can be enhanced by introduction of enzymatic steps. 6e represents ligation of a general detection oligonucleotide. Incorporation of nucleotides comprising a detectable function is illustrated in 6f and solid phase polymerization and subsequent detection by hybridization of a general detection oligo is illustrated in FIG. 6(g).

Specificity

The specificity of the detection of combinations of identifying elements might have to be enhanced if the stringency from the hybridization is insufficient. The hybridization of identification element combinations differs from regular hybridization of single elements. If there are n*2 NAMs (two NAMs per protein) and $n^2$ array identification element oligonucleotides on the array the different array elements can be referred to as $t_{x,y}$ where x is the identity of one identification element position and y the identity of the other identification element. Thus x and y can be any element between 1 and n. The combination of the arbitrary identifying elements a and b will thus complementary to the array element $t_{a,b}$ but they will also be partially complementary to the array elements $t_{x,b}$ and $t_{a,y}$.

The specificity of the hybridization should substantially ensure that the combination a,b primarily hybridizes to the array element $t_{a,b}$. Cross hybridization might occur to some or all of the array elements $t_{x,b}$ and $t_{a,y}$ to some extent, however. In a complex pool of tag combinations which may have a high dynamic range of the different combinations the discrimination between two species may become difficult. If, for example, the combination a,b is present in 10,000 fold excess over the combination a,c the nucleic acid from the a,b combination might cross hybridize to the array element $t_{a,c}$ which is dedicated for the a,c combination. This specificity problem may be solved by, for example, the introduction of enzymatic discrimination steps.

Enzymatic steps have facilitated specific detection of individual nucleotide sequences in the human genome by, for example, utilization of a ligase (see Landegreen et al. *Science* 241, 1077-1080 (1988), Hardenbol et al. *Nat Biotechnol* (2003), Yeakley et al. *Nat Biotechnol* 20, 353-358 (2002), fully incorporated herein by reference), or a polymerase (see Fan et al. *Genome Research* 14, 878-885 (2004), fully incorporated herein by reference). This specificity should be sufficient for a synthetic system where the sequences of the nucleic acid sequences can be designed in silico.

Polymerase Based Discrimination;

To increase the selectivity with a polymerase the hybridized nucleic acids can be allowed to serve as primer or template for a polymerase extension reaction including labelled nucleotides. If this is performed with the proper polymerase which lack, for example, 3' exonuclease activity, and the detection of the hybridized molecules depend on this step, the selectivity of detection is enhanced. Thus only nucleic acids which have hybridized to the array and can form a structure which can serve as a substrate for polymerization will be detected (FIG. 6f). This approach has been utilized for microarray based discrimination of single nucleotide variations in human genomic DNA (see Gunderson, K L et. al Nat Genet. 2005 May; 37(5):549-54, fully incorporated herein by reference).

Ligation Based Discrimination:

To increase the selectivity of detection by ligation the hybridized nucleic acid can be allowed to act as a template or substrate for ligation. The detectable function can be added on a third oligonucleotide which can be joined to the surface complex by ligation. Only if the hybridization event yields a structure which together with the third oligonucleotide, forms a substrate for ligation, will detection be mediated. The ligation may be performed at the 5' end, the 3' end, or both ends of the hybridizing nucleic acid (FIG. 6e).

Ligation and Polymerization Based Specificity Enhancement.

Ligation can also be used in conjunction with polymerization to permit specific detection. If the identifying elements are hybridized so that a circular structure is formed where the 5' and 3' end are in juxtaposition to each other, these two ends can be joined by a ligase to form a circular nucleic acid template in the array. This circular nucleic acid can then serve as a template for polymerization from the array nucleic acid 3' end. If a processive nucleic acid polymerase is used, for example, phi 29 polymerase, a concatemeric polymerization product of several copies of the nucleic acid circle can be produced (see Hatch, A et al Genet Anal. 1999 April; 15(2): 35-40, fully incorporated herein by reference). These copies can then be detected by hybridization of an oligonucleotide attached to a detectable function which hybridizes to the sequence between the identification sequences. This approach only yields signal output if a ligation substrate is formed (FIG. 6g). Other non-limiting examples of ligation approaches which could be used in combination with polymerization are gap fill and subsequent ligation as described in Lizardi et al. *Nat Genet* 19, 225, 232 (1998), or invader cleavage and subsequent ligation as described in Lyamichev et al, *Science* 260, 778-783 (1993).

Sequencing Based Approaches

Sequencing based approaches retrieve the nucleotide sequence of the two identifying elements. These approaches yield a very high complexity of information and thus relatively few nucleotides need to be sequenced to enable identification of a unique element. For example the complexity of five nucleotides is $4^5$=1024 different unique sequences. Thus if sequencing approaches are used very short identifying elements can be utilized. The length of the element used for identification can be adjusted to suit the complexity of the library being investigated. Identification of two different tags in a library of 1000 members and $10^6$ combinations would require sequencing of at least 10 nucleotides per interaction, and five nucleotides per MOI.

However, when sequencing complex pools of nucleic acids, measures have to be taken to isolate the individual molecules or cloned products thereof. This can be done with conventional techniques like molecular cloning into bacteria and subsequent Sanger sequencing. The sequencing of molecular identification sequences of approximately 10 nucleotides can be speeded up significantly by using approaches similar to serial analysis of gene expression (SAGE) where short sequences are joined together before sequencing and several identifying elements can be sequenced in one sequence read. Sequencing of complex pools can also be performed by high throughput approaches like the 454 platform (www.454.com). This approach includes emulsion based clonal PCR amplification and subsequent sequencing on a solid phase. Approaches like this permit very high throughput analysis of the readout.

Depending on the possible readout length these approaches may be combined with SAGE like polymerization of paired identification elements. Solid phase sequencing of the joined tag motifs or possibly concatemeric products thereof would permit information retrieval of the interaction frequency in digital form. However, the sequences combined by the interaction have to be significantly more salient than the background frequency, otherwise the majority if the sequences retrieved will only be random combinations. Sequence based detection of an interaction which is 1000 fold less frequent than another will require sequencing of 1000 identical sequences of the frequent one per copy of the rare one.

Interactor Based Detection

In some situations nucleic acid based amplification of the NAM might not be desired. The different combinations of interactors may then be analyzed directly. One advantage of this is that other identification moieties than the actual nucleic acid could be used or the MOIs may be identified directly. Nonetheless, the readout approach requires identification of at least two separate pieces of information from the associated interactors.

One way of retrieving information from two different species is utilization of a nucleic acid tag array for hybridization of the combinations. In this approach the array would only contain individual tags on the array. Thus if there are n identifiers in the library the array would consist of n spatially separated oligonucleotides. Subsequent to the NAM association and filtering, which could include selection for combined NAMs, the complex of associated interactors is hybridized to the array. The localization of the interactor complexes will reveal the identity of one of the members and the second member is identified by a separate tag moiety, which may be of another nature than nucleic acid. For example, if fluorescent readout is chosen the second tag could be decoded with sequential combinatorial hybridization as described in Gunderson et al., *Genome Research* 14, 870-877 (2004) disclosed fully herein by this reference.

Another approach could be to identify the second tag by matrix assisted laser desorption/ionisation time of flight mass spectrometry (MALDI TOF MS). According to this method, the identification elements in the NAMs would include molecular "tags" which could be identified with this approach. These tags would preferentially be non nucleic acid molecules associated with the NAMs. Depending on the nature of the MOIs these molecules could be identified by MALDI TOF MS directly without the utilization of a separate molecule for the detection.

EXAMPLES

The following examples are intended to illustrate specific embodiments of the present invention and should not be construed as limiting the invention as defined by the claims. All detection schemes encompassed within the scope of the present invention include combinatorial association of NAMs.

Example 1

Affinity Interactions

This example illustrates embodiments directed to detecting affinity interactions.

The individual proteins to be investigated are produced by recombinant expression and purified. These proteins serve as MOIs in the library and are coupled with NAMs to form interactors.

Figure 1:
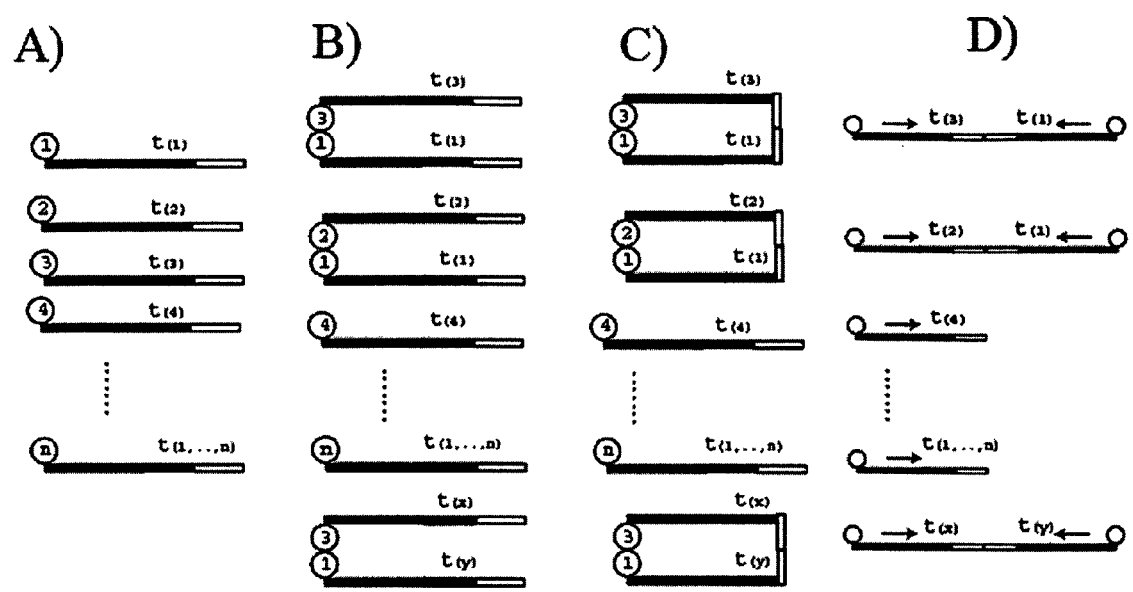
FIG. 1
Figure 2:
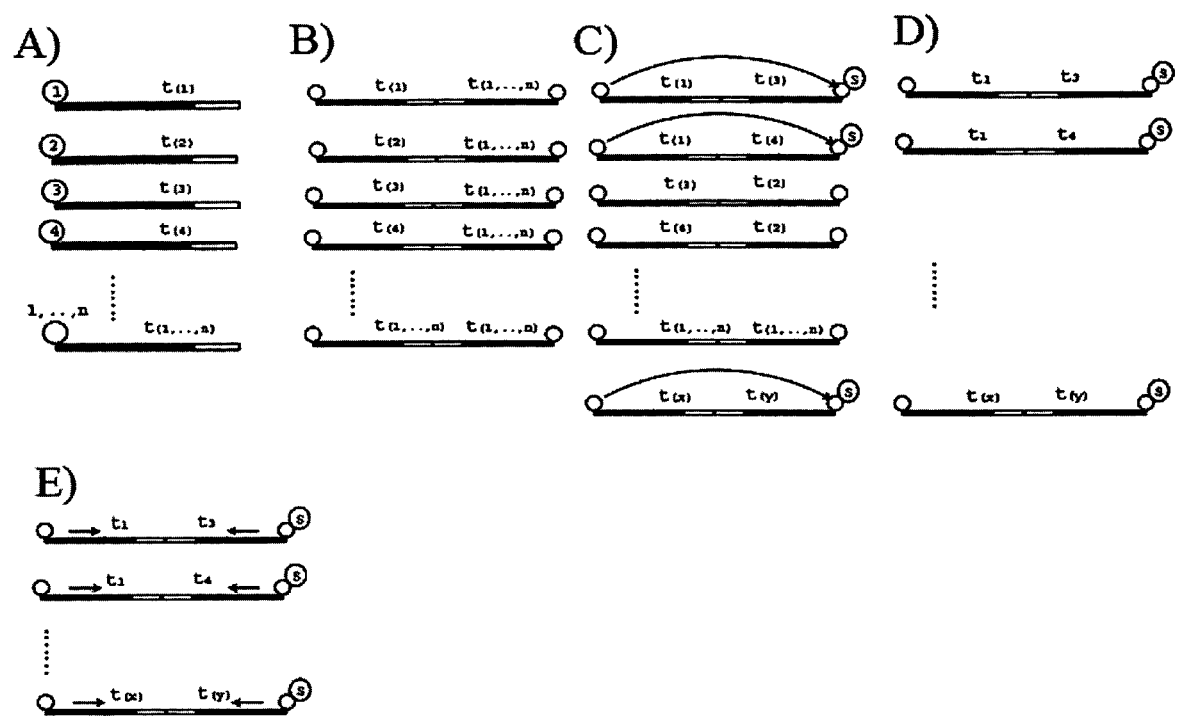
Figure 3:
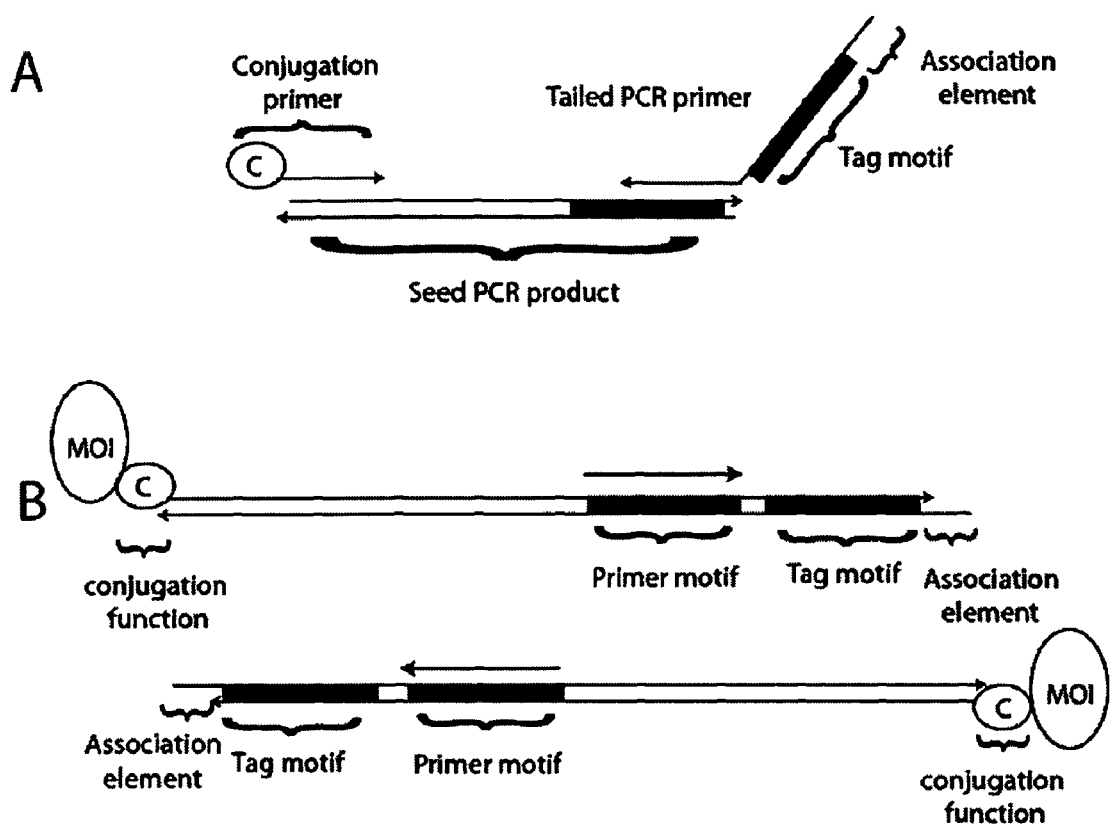

The NAMs are double stranded DNA molecules and comprise a primer motif, a nucleic acid identification sequence and an association sequence. To enable amplification of all intra-library combinations, there are two sub populations of proteins created, one with the forward PCR primer and one with the reverse primer in their respective NAMs (FIG. 3). The nucleic acid identification elements in the two sub-populations comprised by the same protein are not identical, thus each protein is "encoded" by two nucleic acid identification elements in the library.

The individual NAMs are synthesized from two generic PCR products which comprise the general primer motif and spacer sequence. The nucleic acid identification sequence is introduced by performing a second PCR on the generic PCR product with where one primer contains a conjugation function and the other a 5' tail encoding the nucleic acid identification element and the association element.

The coupling function is performed by a sticky end which is created by restriction enzyme digest. The protruding end is created by utilizing a restriction endonuclease which produces a non-palindromic protruding end. The NAMs encoding the forward primer are designed to have one polarity of the protruding end and the NAMs encoding the reverse primer are designed to have the complementary protruding end. The design permits association of several identical NAMs to one MOI without homo-ligation between the NAMs. The individual NAM subtypes are gel purified and associated with the MOI by the conjugation element in one of the primers. The proteins are recombinantly expressed with the IMPACT system from New England Biolabs and the conjugation function of the NAM PCR product is a Cysteine residue. C-terminal fusion of the protein in the IMPACT system generates a $SO_3^-$ group at the N-terminal of the protein which then can be specifically conjugated to the Cysteine group on the NAM. However IMPACT may perform poorly on certain members and additional approaches for conjugation may also be utilized to include all desired proteins.

Subsequent to interactor synthesis by individual coupling of the PCR product derived NAMs to the proteins, the individual interactors are pooled in 1×PBS with inclusion of bovine serum albumin and polyadenine. The interactors are allowed to affinity interact and are subsequently ligated by addition of a ligase mix containing ATP, T4 DNA ligase TRIS HCl pH 7.5 and $MgCl_2$. Following ligation the library is heated to deactivate the ligase and an aliquot of the library is transferred to a PCR reaction. PCR is performed with one biotinylated primer and one Cy3 labelled primer. Subsequent to PCR amplification the fluorescent strand is purified by immobilization of the PCR product on dynabeads and elution of the fluorescent strand. The elution is mixed with hybridization buffer and co-hybridized to a microarray with a control sample. The control sample is treated with protease degradation before ligation and the fluorescent primer is Cy5 labelled. After hybridization the microarray is scanned and analysed with respect to the fluorescent ratios.

The microarray comprises features with all combinations between tags on reverse primer and forward primer NAMs. Thus if 100 proteins are analysed the number of features is 10,000, representing every library interaction in duplicate.

Example 2

Functional Interactions

This example illustrates construction of a library of interactors and CRCs and detection of a specific enzyme-substrate functional interaction where one MOI acts as an enzyme and a second MOI is the substrate.

Enzyme substrate interactions can be difficult to distinguish with conventional approaches since the enzyme might have low or transient affinity to the substrate. A specific choice of enzyme-substrate pair is kinases and their respective substrates. For screening proteins for kinase and kinase substrate properties a library of interactors is constructed where the MOIs of the library are potential kinases and substrates respectively.

Figure 4:
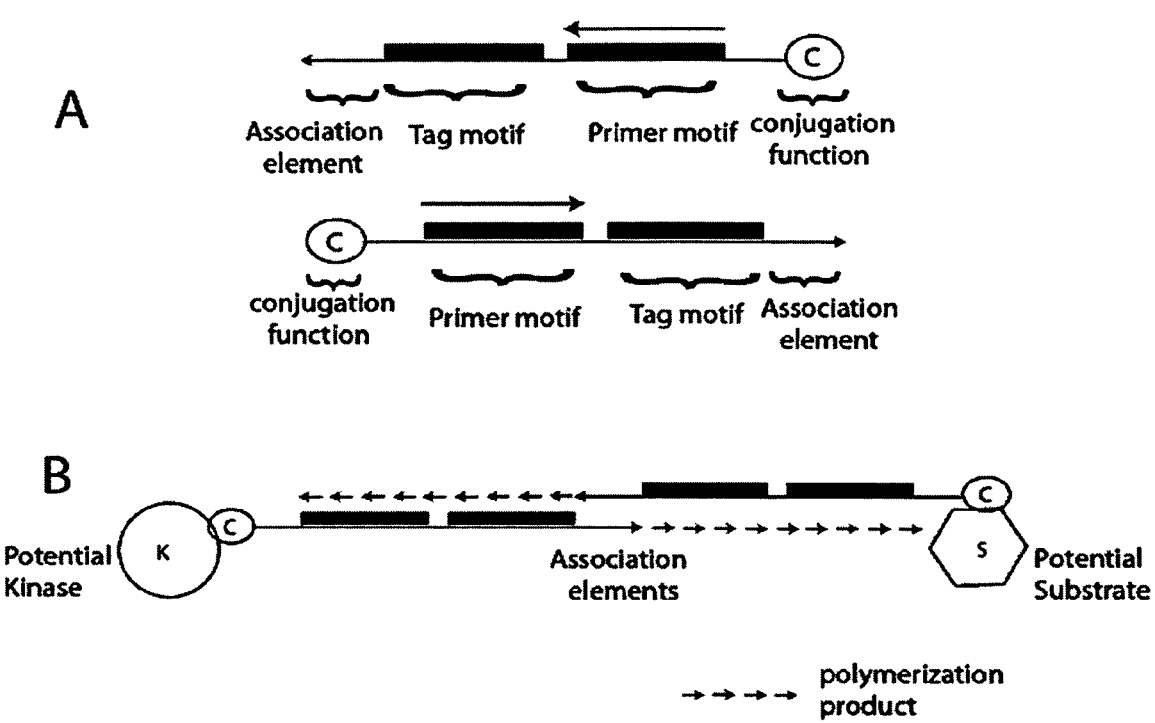

The interactor library comprises two sub-populations, the first comprising potential kinase MOIs and the second comprising potential substrate MOIs. Each sub-population of a potential kinase is conjugated to the 5' end of a oligonucleotide subset comprising the forward primer motif for downstream amplification, the association element in the 3' end of the oligonucleotide and one of a plurality of nucleic acid identification elements. Each sub-population of a potential substrate is conjugated to the 5' end of an oligonucleotide comprising the downstream reverse primer motif, an association element in the 3' end of the oligonucleotide and one of a plurality of nucleic acid identification sequences (FIG. 4).

The NAM association function is a motif for polymerase assisted association at the ends of the oligonucleotides which are not conjugated to the protein. The 3' sequences are designed to be complementary and brings the oligonucleotides comprising the forward primer and the reverse primer together. Upon polymerisation association is stabilised and the respective tags and PCR primers are encoded into the same nucleic acid molecule. The kinases and substrates are proteins and the conjugation between these proteins and their respective oligonucleotides are mediated by expression of the proteins by the IMPACT system and conjugation of oligonucleotides with a Cysteine residue. However proper interactor synthesis may require different expression and conjugation approaches depending on the nature of the protein.

Following interactor synthesis CRCs are stabilized by the addition of a polymerase, nucleotides and the appropriate reaction conditions. 20 nt of the oligonucleotide 3' ends of the two interactor sub populations are complementary and subsequent to hybridization the oligonucleotides serve as both polymerisation templates and substrates respectively. The polymerisation encodes the two identification sequences joined by the hybridisation into one nucleic acid molecule and also stabilise the hybridization of the oligonucleotides further. Polymerisation is achieved by addition of klenow fragment exonuclease deficient polymerase, nucleotides and the appropriate reaction buffer.

The interactors are associated through polymerization to form CRCs and the library is diluted so that the concentration of CRCs becomes significantly lower than the relative concentrations between the interactors in the CRC. To regulate the kinase activity apyrase is added to the library before activation of kinase activity by ATP addition. The appropriate relative concentrations of apyrase and ATP might have to be titrated depending on the kinase activity screened for. The apyrase will degrade the ATP added to the CRC library and thus provide a temporal limitation of kinase activity. Subsequent to activation, the library of CRCs is affinity purified with an antibody specific for a phosphorylated amino acid or amino acid sequence. The library can be split into subsets which are investigated with separate affinity reagents. The selected library is then eluted and an aliquot is amplified by PCR comprising one Cy3 labelled primer and one biotinylated primer. The PCR product is immobilized on streptavidine beads and the fluorescent strand is eluted and co-hybridized to a microarray with a control PCR Cy5 labelled product derived from a library which has not been affinity purified. The microarray contains features which are complementary to all kinase and substrate tag combinations in the library, representing all kinase and substrate interactions between the two libraries.

Example 3

Reaction Discovery

In one specific embodiment screening for reactivity between molecules is provided. A library of molecules is subsequently screened for formation of chemical bonds between the library molecules. The procedure is similar to discovery of affinity interactions, however, in this embodiment, the interaction results in a covalent bond between the molecules. The embodiment enables reactivity screening in different reaction conditions and/or in the presence of catalysts.

The molecules of interest are each tagged with a single stranded DNA NAM to form the interactor library. Two sub types of interactors are constructed, comprising the same molecules of interest, one with free NAM oligonucleotide 3' ends and one with free NAM oligonucleotide 5' ends. These are constructed so that any free 3' end can be joined with any free 5' end by the addition of a DNA oligonucleotide template, complementary to each of the oligonucleotide sub types, by the addition of a ligase and under the appropriate reaction conditions. Each subtype also comprises one PCR primer motif. Oligonucleotides with free 5' ends comprise the forward primer and oligonucleotides with free 3' ends comprise the reverse primer. All DNA NAM oligonucleotides also comprise one unique sequence element for identification.

Ten different molecules of interest are investigated for reactivity in three different reaction conditions, thus there are 10*10=100 different possible reactions, each interrogated in three different reaction conditions.

The 10 interactors comprising NAMs with identical association elements are pooled to form two populations, one comprising 10 interactors with free 3' ends one and comprising 10 interactors with free 5' ends. These pools are subsequently mixed. The interactors are incubated in concentrations of 10-100 nM to allow the chemical reaction to occur. Subsequently the reacted library is diluted down and the template oligonucleotide is added in high concentration together with a ligase mixture. Since the library is screened for formation of covalent bonds, the interaction will not be effected by dilution subsequent to the reaction, however the dilution will reduce the random association. An aliquot of the ligation reaction is transferred to a PCR reaction where the reverse primer contains a 5' biotin modification and the forward primer a 5' Cy5 label. The PCR products are then hybridized to a tag microarray containing all different tag combinations. The hybridization to the microarray is designed according to FIG. 6(a).

Ten different molecules of interest are investigated, $M_1$, $M_2$, ..., $M_{10}$. These molecules are used to create 20 different interactors divided into two pools; one pool with free 3' ends and one with free 5' ends. Each molecule of interest is incorporated in two separate interactors and the identifying sequence elements in these interactors are not identical. The reaction between two molecules of interest will promote intra molecular joining of the respective NAMs during the ligation step. These associated oligonucleotides are then detected by microarray analysis. The microarray comprise 100 different features, each feature representing a combinations between two different tags. All interactions except the homo interactions are represented by two tag combinations on the tag microarray. Subsequent to microarray detection the signal intensity of the microarray features is compared within the microarray and between experiments with different reaction conditions. Three different reaction conditions are investigated, one comprised only of reaction buffer, one comprised of reaction buffer and inclusion of a chemical catalyst, and the last one comprising reaction buffer and a enzyme catalyst, which is presumed to enable reactions between the current substrates.

Figure 7:
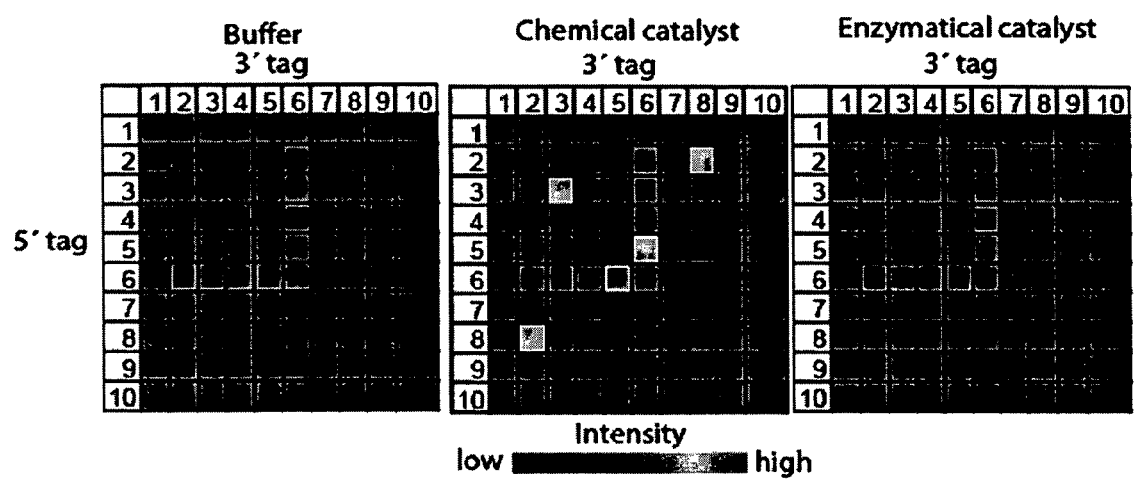

Results:

Results are illustrated in FIG. 7. The figure schematically illustrates a microarray comprising tags complementary to combinations of identification sequence elements. The tags are designated 1 to 10 where tag 1 corresponds to the interactor comprising molecule of interest $M_1$ and so forth. Thus the interactions between two molecules can be deducted from the signal intensity of the respective tag combination. In reaction buffer $M_6$ reacts weakly with molecules of interest $M_2$ through to $M_6$, the last interaction representing an homo interaction. When a chemical catalyst is added reactions occur of moderate intensity between $M_2$-$M_8$, $M_6$-$M_5$, and $M_3$-$M_3$, the last one also representing a homo interaction. When the chemical catalyst is exchanged to an enzymatic one reaction of high intensity occur, $M_9$-$M_6$. The relative reaction efficiencies of the reactions can be interpreted from the array intensities, where a high intensity corresponds to an efficient reaction.

Example 4

Enhancement for Microarray Analysis

To facilitate detection of associated oligonucleotides the nucleic acid to be analyzed may be modified to suit the read-out platform. This modification may include, e.g., modifying enzymes or biochemical modification. In the specific case of tag microarray mediated detection it is desirable to hybridize single stranded DNA. Non limiting examples of generation of single stranded DNA include: amplifying the associated oligonucleotides with RCA which produces a single stranded amplification product comprised of concatemeric amplicon repeats; and single stranded DNA generation subsequent to PCR amplification by, e.g., utilization of one biotinylated primer and streptavidine affinity purification, PCR with one phosphorylated primer and subsequent lambda exonuclease treatment or performing PCR with one primer in excess, also known as asymmetric PCR or Linear After The exponential (LATE) PCR.

Depending on the qualitative design of the microarray detection, the single stranded DNA may be further modified by, e.g, biochemical or enzymatic modification. One specific example of quantitative design is the introduction of a ligation step involving two identification elements on the tag array to form a circular nucleic acid. To enable ligation of the two identification elements to the microarray tag oligonucleotide, a nucleic acid has to be generated that comprises one identification element in the 3' end and one in the 5' end. Downstream of single stranded DNA generation the single stranded DNA may be cleaved with a restriction enzyme next to the identification elements. Restriction enzyme digestion of single stranded nucleic acid may be achieved by hybridization of oligonucleotides comprising the restriction enzyme recognition sequence complementary to the amplification products. In one specific embodiment the enzyme comprises a type IIS restriction endonuclease and in a further specific embodiment the Type IIS restriction enzyme comprises MlyI.

One general design embodiment of the NAMs provides an associated oligonucleotide, downstream of association, comprising the association sequence in the middle flanked by two identification elements which, in turn, are flanked by general sequence in which specific examples can be utilized for amplification by, e.g., PCR or RCA. The associated oligonucleotide may be enhanced to comprise a single stranded amplification product by, for example, the non limiting methods described above.

This single stranded amplification product may then comprise the association sequence in the middle flanked by two identification elements which in turn are flanked by a general sequence (FIG. 8). The general sequence may be designed to comprise the recognition sequence for a restriction enzyme, more specifically a type IIS restriction endonuclease, and in a more specific example comprises the type IIS restriction enzyme, MlyI. In one specific embodiment of generating a single stranded nucleic acid comprising the identification elements in the 3' and 5' ends, the nucleic acid may be designed so the restriction enzyme cleavage occur right between the general sequence contacted by the hybridizing oligonucleotide and the single stranded identification element. In a very specific embodiment, the restriction enzyme comprises MlyI. This results in single stranded nucleic acid with a general sequence in the middle and the identification elements in the 3' and 5' ends.

This nucleic acid may be hybridized and/or ligated to a tag microarray complementary to the identification elements, to form a circular nucleic acid as illustrated in FIG. 5(c). If the nucleic acid is ligated to the tag microarray to form a circular nucleic acid the structure may serve as substrate for RCA amplification. In a specific embodiment, RCA is primed by the microarray tag oligonucleotide and in a more specific embodiment the polymerase is the phi29 polymerase.

Example 5

This example demonstrates that encoding interactors with unique tags and detecting the combinations formed therefrom on a combinatorial array may resolve all interactions within a library. A library of interactors is provided and association of a defined library subset is detected by readout of the respective tag combinations. MOIs are thiol groups. Thiol groups can be induced to dimerize pair-wise and form covalent bonds. This may be compared to a reaction screen where reactive compounds are identified or it can be viewed as formation of an affinity interaction with infinite affinity.

Experimental Design

The application of resolving pair wise reacted groups within an interactor library is exemplified. Formation of a covalent bond is interrogated within a library. Dimerization of thiol groups serves as an example. Oligonucleotides with thiol groups will dimerize pairwise if mixed and subsequently allowed to react. Five oligonucleotides with association elements in the 3' end and 5 oligonucleotides with association elements in the 5' end are employed. Two of the 3' arms and 2 of the 5' arms are equipped with thiol groups. Subsequent to dimerization interacting MOI are identified by association of the respective NAMs by ligation (FIG. 5a). The ligation joins the two tag motifs encoding the thiol groups. The ligated product can also serve as amplification template for PCR, enabling selective amplification of the ligated NAMs. Subsequent to the PCR single stranded DNA is generated by one biotinylated primer and streptavidine support. The buffer for the single stranded DNA is changed by a G50 column. The single stranded DNA is then modified to have the two tag motifs in the ends. This is accomplished by cleaving off the PCR primer sites next to the identification tags. (FIG. 8) Cleavage is mediated by annealing two oligonucleotides directing the restriction enzyme cleavage and then adding the restriction enzyme MlyI. The cleaved product will have the identifying elements in the 3' and 5' end respectively. These are then added to a microarray comprising oligonucleotides complementary to the tag combinations. The reporter molecules created by the cleavage hybridize to the array oligonucleotide with the correct tags similar to FIG. 6(c). The hybridized DNA is then ligated and a circular substrate forms which can serve as a template for rolling circle replication and detected by general detection reagents (FIG. 6(g)).

Experimental Procedure a. Library Construction via dimerization of thiol modified oligonucleotides: all oligonucleotides are obtained from commercial vendors, including oligonucleotides with thiol groups for reaction screening or amine groups for array manufacturing. Each oligonucleotide comprises one unique tag element and one of two primer sites. A selected subset of the oligonucleotides are also equipped with thiol groups enabling selective dimerization. The mixture comprising thiol modified oligonucleotides is dimerized by addition of 1M DTT, facilitating reduction of the homodimeric oligonucleotides. Subsequent exclusion of the DTT is achieved by a buffer exchange column.

b. Association and selection by ligation and PCR

A total volume of 5 µl comprising 100 pM of the thiolated (NAM-Thiol-D5, NAM-Thiol-E5, NAM-Thiol-A3, NAM-Thiol-B3 and non thiolated oligonucleotides (NAM B5, NAM, C5, NAM F5, NAM C3, Nam D3, NAM E3) is mixed to constitute a final volume of 50 µl comprising 1×PCR buffer (available from Invitrogen, Norway), 5 pmol of each PCR primer (FWDprime, REWprime), 1.5 U Taq platinum (available from Invitrogen, Norway), 3 mM $MgCl_2$, 80 mM ATP, 100 nM of the oligonucleotide LigA, 200 nM dNTP and 1 U T4 DNA ligase. The mixture is incubated at 95 C for 2 min and then cycled 30 times between 60 C and 95 C.

c. Analysis of the two identification sequences in the associated oligonucleotides Generation of Single Stranded DNA Five µl of Streptavidine coated Dynabeads M-280 (Invitrogen, Norway) is washed twice in B&W buffer (1M NaCl, 0.5 mM EDTA, 5 mM Tris-HCl pH 7.5) and subsequently the reaction is added to the beads and allowed to bind for 10 minutes. The beads are then washed twice in 100 µl of B&W buffer. Subsequent to washing the beads are incubated with 5 µl 0.1M NaOH for 5 minutes. The NaOH supernatant is subsequently removed and mixed with 5 µl 0.1M HCl and 5 µl 0.1M TRIS-HCl pH8.

Buffer Exchange

The eluted and neutralized DNA is added to a G50 column (available from General Electric) and purified according to the manufacturers instructions.

Restriction Enzyme Cleavage

10 µl of the column eluate is mixed with 2 µl of S8 buffer (20 mM Tris Ac pH 8, 50 mM KAc, 10 mM $(NH_4)_2SO_4$, 10 mM $MgAc_2$, 1 mM DTT) 5 U MlyI (available from New England Biolabs), 10 pmol of the oligonucleotides REVprime and MlyIRE, 2 µg of BSA and 5.5 µl of dd$H_2O$. The reaction is first incubated for 1 h at 37° C. and then at 75° C. for 15 min.

Microarray Manufacturing

Microarrays are manufactured by a GMS 417 microarray printer. The oligonucleotides are printed on Codelink™ slides (available from General Electric) in a solution comprising 10 µM oligonucleotide, 150 mM $NaCO_3$ pH9, and 0.05% SDS. After printing, the slides are incubated for at least 1 h in a humid chamber and then blocked with 30 ml 70% EtOH, 70 ml 1×PBS and 0.235 g $NaBH_4$. Slides are washed and dried by centrifugation.

Ligation to Microarrays

Following incubation the reaction is mixed with 3 µl 10× Ampligase Buffer (Epicentre), 25 µg BSA, 5 U Ampligase (Epicentre) and 23.5 µl dd$H_2O$. The mixture is added to a microarray slide comprising the oligonucleotides Tag3A5B; Tag3A5C, Tag3A5D, Tag3A5E, Tag3A5F, Tag3B5C, Tag3B5D, Tag3B5E, Tag3B5F, Tag3C5D Tag3C5E, Tag3C5F, Tag3D5E, Tag3D5F, Tag3E5F. The reaction is incubated on the slide in a silicon rubber chamber (Genome Res. 2000 July; 10(7):1031-42.) based on a 96 well format at 50° C. over night. The slide is then washed in 0.75×TNT buffer (75 mM Tris-HCl, pH 7.5, 0.1125 M NaCl, and 0.0375% Tween 20) rinsed in 0.1×SSC and dried by centrifugation.

Rolling Circle Amplification and Detection on Microarrays

A reaction mixture comprising 1×Phi29 buffer (available from Fermentas), 25 µg BSA, 0.2 mM dNTP, 10 U Phi29 in the final volume of 50 µl was added to the slide and incubated for 1 h at 37° C. The slide is then washed in 0.75×TNT buffer, rinsed in 0.1×SSC and dried by centrifugation.

The slide is incubated with 50 µl comprising 2×SSC, 0.1× SDS and 10 nM of the oligonucleotide DET at room temperature. The slide is then washed in 0.75×TNT buffer, rinsed in 0.1×SSC and dried by centrifugation.

Data Acquisition and Analysis

The slide is scanned in a Genepix™ scanner and the data acquired by Genepix pro 5.0 exported and analysed in Microsoft Excel® (Microsoft Office 2003). Signal-to-Noise was calculated by dividing the Feature signal with the average signal of all features.

d. Results

Figure 9:
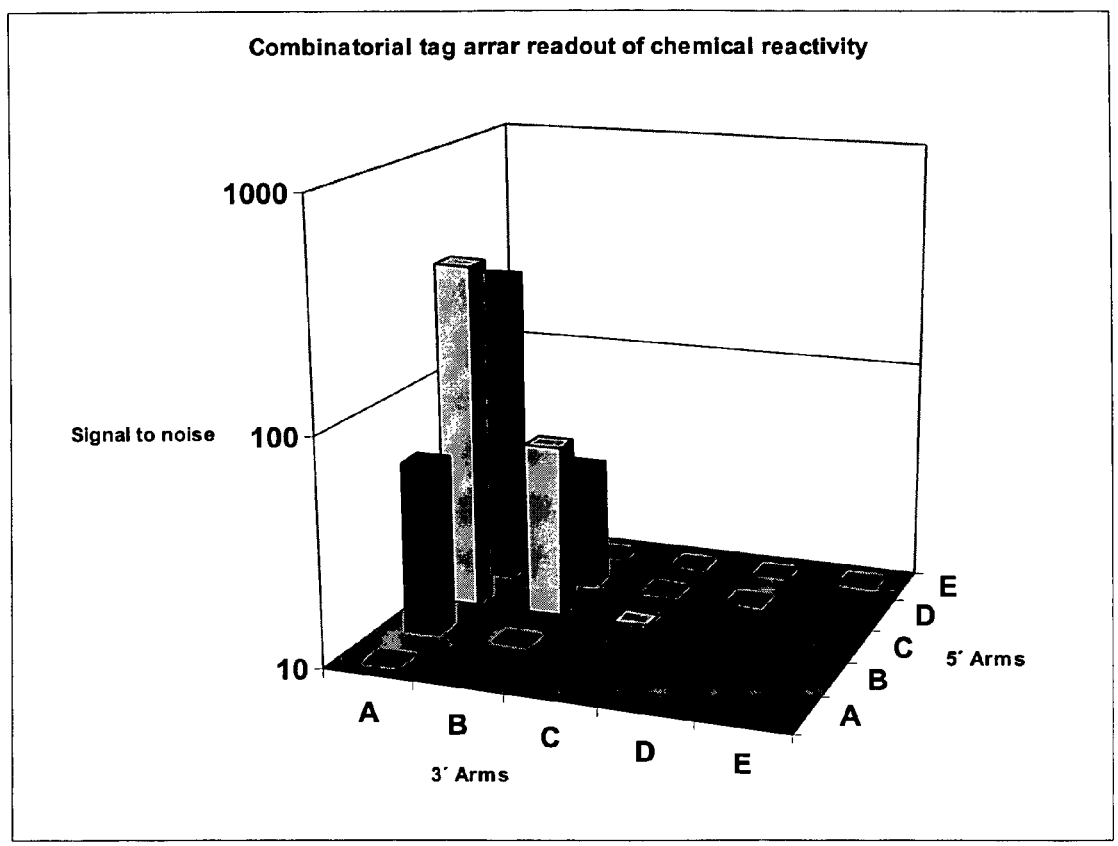

The microarray features are represented in FIG. 9. The grid represents the combination of the different oligonucleotide tag combinations. The four microarray features representing combinations of the interactors equipped with thiol groups show increased signal to noise, due to their interaction. The other tag pairs represented in the library and on the array display low signal to noise, however significant background is visible in one feature due to cross hybridization of the detection oligonucleotide.

The invention claimed is:

1. A method of detecting functional interactions between at least two molecules of interest, the method comprising:
   a. forming a plurality of interactors by coupling each molecule of interest with at least one nucleic acid moiety, the nucleic acid moiety comprising an identification sequence element and an association element;
   b. forming a plurality of cis-reactive cells wherein a cis-reactive cell comprises at least two interactors bound in proximity to one another by an associated oligonucleotide formed from the association between at least two nucleic acid moieties, wherein the associated oligonucleotide comprises at least two identification elements derived from the at least two nucleic acid moieties;
   c. subjecting the plurality of cis-reactive cells to conditions which stimulate a desired functional interaction having a detectable trace;
   d. selecting all cis-reactive cells exhibiting the detectable trace; and
   e. subjecting the associated oligonucleotides from the cis-reactive cells selected in step (d) to an analysis that permits detection of the at least two identification sequence elements.

2. The method of detecting functional interactions between at least two molecules of interest as recited in claim 1, wherein selecting all cis-reactive cells exhibiting the detectable trace is accomplished via selective separation or selective detection of the cis-reactive cells.

3. The method of detecting functional interactions between at least two molecules of interest as recited in claim 2, wherein selecting all cis-reactive cells exhibiting the detectable trace is accomplished by affinity purification.

4. A method of detecting functional interactions between at least two molecules of interest as recited in claim 1, further comprising enhancing the selected associated oligonucleotides by PCR amplification.

5. A method of detecting functional interactions between at least two molecules of interest as recited in claim 1, wherein coupling is covalent or noncovalent.

6. A method of detecting functional interactions between at least two molecules of interest as recited in claim 5, wherein coupling is covalent.

7. A method of detecting functional interactions between at least two molecules of interest, as recited in claim 1, wherein at least one molecule of interest comprises a protein, a protein domain, a peptide, a peptoid, a functional enzyme, a small molecule, a polymer, a non-proteinaceous cellular product, a virus particle, a cell metabolite, a lipid, a carbohydrate, a nucleic acid, an inorganic compound, a reactive compound, or any combination thereof, however, wherein not all molecules of interest are nucleic acids.

8. A method of detecting functional interactions between at least two molecules of interest, as recited in claim 7, wherein at least one molecule of interest comprises at least one protein.

9. The method of detecting functional interactions between at least two molecules of interest as recited in claim 8, wherein the protein is an expression product of a nucleic acid molecule, and further wherein at least some of the plurality of interactors are formed by coupling the protein with a nucleic acid moiety comprising an identification sequence element derived from the nucleic acid molecule.

10. A method of detecting functional interactions between at least two molecules of interest, as recited in claim 7, wherein the at least two molecules of interest comprises at least one protein and at least one nucleic acid.

11. A method of detecting functional interactions between at least two molecules of interest, as recited in claim 1, wherein detecting further comprises quantifying the functional interactions.

12. A method of detecting functional interactions between at least two molecules of interest, as recited in claim 1, wherein the analysis comprises high throughput screening.

13. The method of detecting functional interactions between at least two molecules of interest as recited in claim 12, wherein the high throughput screening comprises a micro array analysis.

14. The method of detecting functional interactions between at least two molecules of interest as recited in claim 1, wherein the analysis comprises nucleic acid sequencing.

15. The method of detecting functional interactions between at least two molecules of interest as recited in claim 14, wherein the analysis comprises sequencing by synthesis.

16. The method of detecting functional interactions between at least two molecules of interest as recited in claim 1, wherein association is via ligation.

17. The method of detecting functional interactions between at least two molecules of interest as recited in claim 1, wherein association is via polymerization.

18. The method of detecting functional interactions between the at least two molecules of interest as recited in claim 1, wherein the conditions for stimulating the functional interaction between the at least two molecules of interest comprises manipulating conditions to maximize cis reactivity and to minimize trans reactivity between the at least two molecules of interest.

19. The method of detecting functional interactions between at least two molecules of interest as recited in claim 12, wherein the selective detection comprises labeling the cis-reactive cells with an affinity reagent.

20. The method of detecting functional interactions between at least two molecules of interest as recited in claim 2, wherein the selective detection comprises introducing a modified molecule wherein the modification permits the selective detection.

* * * * *

UNITED STATES PATENT AND TRADEMARK OFFICE
CERTIFICATE OF CORRECTION

| | | |
|---|---|---|
| PATENT NO. | : 7,883,848 B2 | Page 1 of 1 |
| APPLICATION NO. | : 11/483825 | |
| DATED | : February 8, 2011 | |
| INVENTOR(S) | : Ericsson | |

It is certified that error appears in the above-identified patent and that said Letters Patent is hereby corrected as shown below:

Column 44, line 13, change "12," to --2,--

Signed and Sealed this
Twenty-second Day of November, 2011

David J. Kappos
*Director of the United States Patent and Trademark Office*